US005670477A

United States Patent [19]
Poduslo et al.

[11] Patent Number: 5,670,477
[45] Date of Patent: Sep. 23, 1997

[54] METHOD TO ENHANCE PERMEABILITY OF THE BLOOD/BRAIN BLOOD/NERVE BARIERS TO THERAPEUTIC AGENTS

[75] Inventors: Joseph F. Poduslo, 5719 St. Mary's Dr. NW, Rochester, Minn. 55901; Geoffrey L. Curran, 629 23rd St. NE, Rochester, Minn. 55906

[73] Assignees: Joseph F. Poduslo; Geoffrey L. Curran, both of Rochester, Minn.

[21] Appl. No.: 425,576

[22] Filed: Apr. 20, 1995

[51] Int. Cl.[6] .................................................. A61K 23/02
[52] U.S. Cl. ................................................................ 514/2
[58] Field of Search ...................................................... 514/2

[56] References Cited

U.S. PATENT DOCUMENTS

| 3,903,262 | 9/1975 | Pappenhagen et al. | 424/85 |
| 4,863,730 | 9/1989 | Karpas | 424/86 |
| 5,260,308 | 11/1993 | Poduslo et al. | 514/21 |

OTHER PUBLICATIONS

Barnett et al., "Humanβ Nerve Growth Factor Obtained from a Baculovirus Expression System has Potent in Vitro and in Vivo Neurotrophic Activity", *Experimental Neurology*, 110, 11–24, (1990).

Baskin et al., "Insulin in the Brain", *Ann. Rev. Physiol.*, 49, 335–347, (1987).

F. Hefti et al., "Function of Neurotrophic Factors in the Adult and Aging Brain and Their Possible Use in the Treatment of Neurodegenerative Diseases", *Neurobiology of Aging*, 10, 515–533, (1989).

Franz Hefti, "Neurotrophic Factor Therapy for Nervous System Degenerative Diseases", *Journal of Neurobiology*, 25, 1418–1435, (1994).

Franz Hefti, "Development of Effective Therapy for Alzheimer's Disease Based on Neurotrophic Factors", *Neurobiology of Aging*, 15, S193–S194, (1994).

Joseph F. Poduslo et al., "Altered Blood–Nerve Barrier in Experimental Lead Neuropathy Assessed by Changes in Endoneurial Albumin Concentration", *The Journal of Neuroscience*, 2, 1507–1514, (Oct. 1982).

Joseph F. Poduslo, "Glycoprotein Molecular-Weight Estimation Using sodium dodecyl Sulfate–Pore Gradient Electrophoresis: Comparison of Tris–Glycine and Tris–Borate–EDTA Buffer Systems", *Analytical Biochemistry*, 114, 131–139, (1981).

Joseph F. Poduslo et al., "Increase in albumin, IgG, and IgM blood–nerve barrier indices in human diabetic neuropathy", *Proc. Natl. Acad. Sci. USA*, 85, 4879–4883, (Jul. 1988).

Joseph F. Poduslo et al., "Macromolecular permeability across the blood–nerve and blood–brain barriers", *Proc. Natl. Acad. Sci. USA*, 91, 5705–5709, (Jun. 1994).

Emanuel Rechthand et al., "Regulation of the Microenvironment of Peripheral Nerve: role of the Blood–Nerve Barrier", *Progress in Neurobiology*, 28, 303–343 (1987).

Michael W. Schwartz et al., "Kinetics and specificity of insulin uptake from plasma into cerebrospinal fluid", *Am. J. Physiol.*, 259, E378–E383, (1980).

Ananda Weerasuriya et al., "Blood–nerve transfer of albumin and its implications for the endoneurial microenvironment", *Brain Research*, 494, 114–121, (1989).

Chemical Abstracts AN 1989:190366, Koenig et al, 1989.

*Primary Examiner*—Keith MacMillan
*Attorney, Agent, or Firm*—Schwegman, Lundberg, Woessner & Kluth, P.A.

[57] ABSTRACT

A method is provided to enhance the ability of a neurologically active compound to penetrate the blood nerve barrier (BNB) or blood brain barrier (BBB), by administration of a conjugate comprising the neurologically active compound linked to a carrier molecule that has been shown to have a substantial permeability coefficient across the BNB and BBB.

21 Claims, 8 Drawing Sheets

METHOD TO ENHANCE PERMEABILITY OF THE BLOOD/BRAIN BLOOD/NERVE BARIERS TO THERAPEUTIC AGENTS

BACKGROUND OF THE INVENTION

The interstitial connective tissue in the peripheral nerve that separates the individual nerve fibers of a vertebrate is referred to as the endoneurium, and can be visualized as an insulative medium in which conductive wires are embedded. Blood vessels in the endoneurium of peripheral nerves are comparable to those of the central nervous system and are lined by a continuous endothelium, made up of capillary endothelial cells, with intercellular tight junctions of high electrical resistance (100 ohm/cm$^2$). Together with the perineurium, a connective tissue sheath immediately surrounding the fascicles of nerve fibers, the vessels form a blood-nerve barrier (BNB) to regulate the microenvironment of the endoneurium of the nerve. The blood-cerebrospinal fluid barrier and the blood brain barrier (collectively the "BBB") are also associated with the tight junctions which adjoin adjacent capillary endothelial cells within the brain and spinal cord, to regulate this microenvironment as well.

The BNB and BBB are effective barriers to both endogenous and exogenously-administered blood components, including peptides, proteins and other large macromolecules, as well as to ions and water-soluble non-electrolytes. This protects the brain or endoneurial microenvironment from rapid changes in the composition of the blood or of the extraneural spaces. Also, alterations in BBB or BNB integrity are implicated in a number of brain and peripheral nerve disorders, such as those caused by diabetes mellitus, toxins, infection and autoimmune disorders.

However, the ability of the BNB and BBB to protect the nervous system from exogenous substances has impeded the development of both diagnostic assays and therapies for a wide variety of neural pathologies and disorders. Thus, a continuing need exists for methods to increase the permeability of the BNB or the BBB to bioactive substances, particularly to bioactive peptides and U.S. Pat. No. 5,260,308, issued to Poduslo and Curran discloses a method to increase the permeability of the BNB or the BBB to bioactive peptides and protein. This method involves the glycation of the bioactive peptides and proteins.

SUMMARY OF THE INVENTION

The present invention provides a method to enhance the ability of a neurologically active compound to penetrate the blood nerve barrier (BNB) or blood brain barrier (BBB). The method comprises parenterally administering to a mammal, preferably a human, in need of treatment with said neurologically active compound, a conjugate consisting of an effective amount of said neurologically active compound linked to a carrier molecule which enhances the permeability of the BNB or BBB to said neurologically active compound. Preferably, the method of the present invention will employ a naturally occurring polyamine as the carrier molecule. Most preferably, the method of the present invention will employ the natural cell metabolites putrescine (PUT), spermidine (SPD) or spermine (SPM) as the carrier molecule.

The present invention is based at least partially on the surprising discovery that, when given parenterally in normal adult animals, polyamine-modified neurologically active compounds not only show enhanced permeability at the BBB and BNB, but retain their biological activity and elicit a response in cells within the nervous system. For example, it was discovered that parenterally administered, polyamine-modified neuronal growth factor (NGF) shows not only enhanced permeability and retention of biological activity, but also is targeted to specific brain regions populated by cholinergic neurons where it elicits an increase in choline acetyltransferase activity in the normal adult animal where the BBB is not compromised.

A wide variety of neurologically active compounds can be transported across the BNB or BBB to affect the central nervous system (CNS) or the peripheral nervous system (PNS) of the mammal to be treated. For example, the neurologically active compound to be utilized in the method of the present invention can be selected from the group consisting of a compound acting at synaptic and/or neuroeffector junctional sites, a compound acting on the central or peripheral nervous systems, an antioxidant (or other free radical scavenger) or a neurotrophic protein. Preferably, the method of the present invention will employ an antioxidant (or other free radical scavenger) or a neurotrophic protein as the neurologically active compound. Additionally, although there could be a plurality of neurologically active compounds linked to any given carrier molecule, and the molar ratio will vary with the particular neurologically active compound employed, preferably, the conjugate comprises about a 1:1 molar ratio of the neurologically active compound and the carrier molecule. Furthermore, in the practice of the method of the present invention, the conjugate is preferably administered in combination with a pharmaceutically acceptable carrier, such as a carrier adapted for parenteral administration. Further, the pharmaceutically acceptable carrier is preferably a liquid vehicle.

The present invention also provides a pharmaceutical composition comprising the above-mentioned neurologically active compound linked to a carrier molecule in combination with a pharmaceutically acceptable carrier. In this embodiment of the invention, the pharmaceutically acceptable carrier utilized is preferably one adapted for parenteral administration. More preferably, the pharmaceutically acceptable carrier is a liquid vehicle. Furthermore, in this embodiment of the invention, the neurologically active compound will preferably be a compound acting at a synaptic and/or neuroeffector junctional site, a compound acting on the central or peripheral nervous system, an antioxidant (or other free radical scavenger), or a neurotrophic protein. More preferably, the neurologically active compound will be an antioxidant or a neurotrophic protein.

The present invention further provides an isolated polyamine-modified neurologically active compound. In this embodiment of the invention, the neurologically active compound will preferably be modified with a polyamine to the extent that an effective amount of the compound crosses the BNB or BBB of a mammal to which the modified compound is administered. In this embodiment of the invention, the neurologically active compound is preferably chosen from the group consisting of a compound acting at a synaptic and/or neuroeffector junctional site, a compound acting in the central or peripheral nervous system, an antioxidant or a neurotrophic protein. More preferably, the neurologically active compound will be an antioxidant or a neurotrophic protein. Furthermore, in this embodiment of the invention, the carrier molecule will preferably be chosen from the group consisting of putrescine, spermidine and spermine.

The selective neuronal loss observed in ALS, Alzheimer's, Parkinson's, cerebral ischemia and other neurodegenerative diseases, coupled with the growing body of evidence that neurotrophic factors have a protective effect against various degenerative lesions, suggests a therapeutic role for a large variety of neurotrophic factors in treating these diseases. Similarly, superoxide dismutase (SOD), brain derived neurotrophic factor (BDNF), and basic fibroblast growth factor (bFGF) have been suggested to have a role in preventing hippocamus neuronal damage following cerebral ishemia. Thus, it is also contemplated that the delivery of the conjugates of the present invention to the nervous system will be a useful therapeutic approach for treating a variety of neurological diseases. Furthermore, while the experiments disclosed describe the three polyamines putrescine, spermidine, and spermine, other naturally occurring polyamines would function in a similar manner and thus are contemplated by the present invention. Similarly, it is probable that this methodology can be extended to other neurologically active compounds than those described below or in the examples.

DETAILED DESCRIPTION OF THE INVENTION

A. Neurologically Active Compounds

Figure 1:
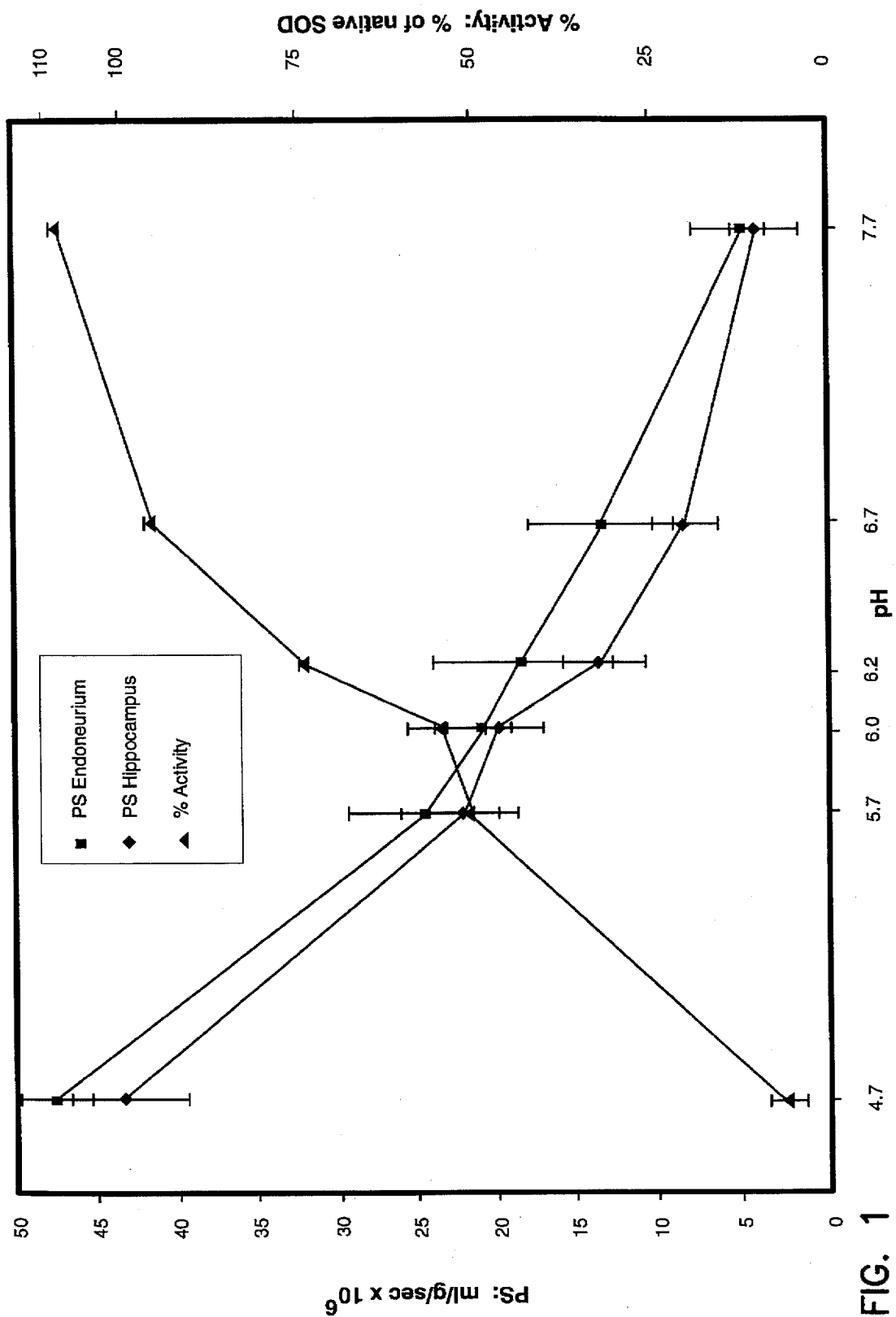
FIG. 1 is a graphical depiction of the relationship between the enzyme activity of PUT-SOD and PS when SOD is modified with PUT at varying pH's.

Neurologically active compounds which can be introduced into the nervous system, i.e., into the endoneurial or brain microenvironment, in accord with the present invention, include any bioactive compound which can be purified and conjugated or cross-linked to the carrier molecule, so that its ability to cross the BNB or BBB is substantially enhanced over the nonconjugated form of the neurologically active compound. As used herein with respect to the conjugated neurologically active compounds useful in the present method, the term "neurologically active" or "neuroactive" means that the neurologically active compound exerts a direct or indirect beneficial therapeutic effect upon introduction into the nervous system, e.g., by stimulating nerve growth or activity, scavenging free radicals, neutralizing a pathogen, relieving pain, affecting a psychological state, inhibiting neoplastic cell growth and the like.

1. Neurologically Active Compounds Acting at Synaptic and Neuroeffector Junction Sites The neurologically active compound useful in the present conjugate may be one that acts at the synaptic and neuroeffector junctional sites; such as a cholinergic agonist, a anticholinesterase agent, catecholamine and other sympathomimetic drugs, an adrenergic receptor antagonist, an antimuscarinic drug, and an agent that act at the neuromuscular junction and autonomic ganglia.

a. Cholinergic Agonists

Examples of suitable cholinergic agonists include, but are not limited to, choline chloride, acetylcholine chloride, methacholine chloride, carbachol chloride, bethanechol chloride, pilocarpine, muscarine, arecoline and the like. See Taylor, P., in *The Pharmacological Basis of Therapeutics*, Gilman, et al., eds., Pergamon Press, New York, 1990, 8th edition, Chapter 6, pp. 122–130.

b. Anticholinesterase Agents

Suitable anticholinesterase compounds are exemplified by the group consisting of carbaril, physostigmine, neostigmine, edrophonium, pyridostigmine, demecarium, ambenonium, tetrahydroacridine and the like. See Taylor, P., in *The Pharmacological Basis of Therapeutics*, Gilman, et al., eds., Pergamon Press, New York, 1990, 8th edition, Chapter 7, pp. 131–149.

c. Catecholamines and other Sympathomimetic Neurologically Active Compounds

Suitable catecholamines and sympathomimetic drugs include the subclasses of endogenous catecholamines, β-adrenergic agonists, α-adrenergic agonists and other miscellaneous adrenergic agonists.

Within the subclass of endogenous catecholamines, suitable examples include epinephrine, norepinephrine, dopamine and the like. Suitable examples within the subclass of β-adrenergic agonists include, but are not limited to, isoproterenol, dobutamine, metaproterenol, terbutaline, albuterol, isoetharine, pirbuterol, bitolterol, ritodrine and the like. The subclass of α-adrenergic agonists can be exemplified by methoxamine, phenylephrine, mephentermine, metaraminol, clonidine, guanfacine, guanabenz, methyldopa and the like. Other miscellaneous adrenergic agents include, but are not limited to, amphetamine, methamphetamine, methylphenidate, pemoline, ephedrine and ethylnorepinephrine and the like. See Hoffman et al., in *The Pharmacological Basis of Therapeutics*, Gilman, et al., eds., Pergamon Press, New York, 1990, 8th edition, Chapter 10, pp. 187–220.

d. Adrenergic Receptor Antagonists

Adrenergic receptor antagonists include the subclasses of α-adrenergic receptor antagonists and β-adrenergic receptor antagonists. Suitable examples of neurologically active compounds that can be classified as α-adrenergic receptor antagonists include, but are not limited to, phenoxybenzamine and related haloalkylamines, phentolamine, tolazoline, prazosin and related drugs, ergot alkaloids and the like. Either selective or nonselective β-adrenergic receptor antagonists are suitable for use in the present invention, as are other miscellaneous β-adrenergic receptor antagonists. See Hoffman et al., in *The Pharmacological Basis of Therapeutics*, Gilman, et al., eds., Pergamon Press, New York, 1990, 8th edition, Chapter 11, pp. 221–243.

e. Antimuscarinic Neurologically Active Compounds

Antimuscarinic drugs are exemplified by the group consisting of atropine, scopolamine, homatropine, belladonna, methscopolamine, methantheline, propantheline, ipratropium, cyclopentolate, tropicamide, pirenzepine and the like. See Brown, J. H., in *The Pharmacological Basis of*

*Therapeutics*, Gilman, et al., eds., Pergamon Press, New York, 1990, 8th edition, Chapter 8, pp. 150–165.

f. Compounds that act at the Neuromuscular Junction and Autonomic Ganglia

Suitable examples of neurologically active compounds that can be classified as compounds that act at the neuromuscular junction and autonomic ganglia include, but are not limited to tubocurarine, alcuronium, β- Erythroidine, pancuronium, gallamine, atracuriam, decamethonium, succinylcholine, nicotine, labeline, tetramethylammonium, 1,1-dimethyl-4-phenylpiperazinium, hexamethonium, pentolinium, trimethaphan and mecamylamine, and the like. See Taylor, P., in *The Pharmacological Basis of Therapeutics*, Gilman, et al., eds., Pergamon Press, New York, 1990, 8th edition, Chapter 8, pp. 166–186.

2. Drugs Acting on the Central Nervous System and the Peripheral Nervous System

The neurologically active compound of the present invention may also be one that acts on the central nervous system (CNS) and peripheral nervous system (PNS), such as nonpeptide neurotransmitters, peptide neurotransmitters and neurohormones, proteins associated with membranes of synaptic vessels, neuromodulators, neuromediators, sedative-hypnotics, antiepileptic therapeutic agents, therapeutic agents effective in the treatment of Parkinsonism and other movement disorders, opioid analgesics and antagonists and antipsychotic compounds.

a. Nonpeptide Neurotransmitters

Nonpeptide neurotransmitters include the subclasses of neutral amino acids—such as glycine and gamma-aminobutyric acid and acidic amino acids such as glutamate, aspartate, and NMDA receptor antagonist-MK801 (Dizocilpine Maleate). L. L. Iversen, *Neurotransmissions*, Research biochemicals Internation, Vol. X, no. 1, Feb. 1994. Other suitable nonpeptide neurotransmitters are exemplified by acetylcholine and the subclass of monoamines—such as dopamine, norepinephrine, 5-hydroxytryptamine, histamine, and epinephrine.

b. Neurotransmitters and Neurohormones - Neuroactive Peptides

Neurotransmitters and neurohormones that are neuroactive peptides include the subclasses of hypothalamic-releasing hormones, neurohypophyseal hormones, pituitary peptides, invertebrate peptides, gastrointestinal peptides, those peptides found in the heart—such as atrial naturetic peptide, and other neuroactive peptides. See J. H. Schwartz, "Chemical Messengers: Small Molecules and Peptides" in *Principles of Neural Science, 3rd Edition*; E. R. Kandel et al., Eds.; Elsevier: New York; Chapter 14, pp. 213–224 (1991).

The subclass of hypothalamic releasing hormones includes as suitable examples, thyrotropin-releasing hormones, gonadotropin-releasing hormone, somatostatins, corticotropin-releasing hormone and growth hormone-releasing hormone.

The subclass of neurohypophyseal hormones is exemplified by compounds such as vasopressin, oxytocin, and neurophysins. Likewise the subclass of pituitary peptides is exemplified by the group consisting of adrenocorticotropic hormone, β-endorphin, α-melanocyte-stimulating hormone, prolactin, luteinizing hormone, growth hormone, and thyrotropin.

Suitable invertebrate peptides are exemplified by the group comprising FMRF amide, hydra head activator, proctolin, small cardiac peptides, myomodulins, buccolins, egg-laying hormone and bag cell peptides. The subclass of gastrointestinal peptides includes such neurologically active compounds as vasoactive intestinal peptide, cholecystokinin, gastrin, neurotensin, methionineenkephalin, leucine-enkephalin, insulin and insulin-like growth factors I and II, glucagon, peptide histidine isoleucineamide, bombesin, motilin and secretins.

Suitable examples of other neuroactive peptides include angiotensin II, bradykinin, dynorphin, opiocortins, sleep peptide(s), calcitonin, CGRP (calcitonin gene-related peptide), neuropeptide Y, neuropeptide Yy, galanin, substance K (neurokinin), physalaemin, Kassinin, uperolein, eledoisin and atrial naturetic peptide.

c. Proteins associated with Membranes of Synaptic Vesicles

Proteins associated with membranes of synaptic vesicles include the subclasses of calcium-binding proteins and other synaptic vesicle proteins.

The subclass of calcium-binding proteins further includes the cytoskeleton-associated proteins—such as caldesmon, annexins, calelectrin (mammalian), calelectrin (torpedo), calpactin I, calpactin complex, calpactin II, endonexin I, endonexin II, protein II, synexin I; and enzyme modulators—such as p65.

Other synaptic vesicle proteins include inhibitors of mobilization (such as synapsin Ia,b and synapsin IIa,b), possible fusion proteins such as synaptophysin, and proteins of unknown function such as p29, VAMP-1,2 (synaptobrevin), VAT1, rab 3A, and rab 3B. See J. H. Schwartz, "Synaptic Vessicles" in *Principles of Neural Science, 3rd Edition;* E. R. Kandel et al., Eds.; Elsevier: New York; Chapter 15, pp. 225–234 (1991).

d. Neuromodulators

Neuromodulators can be exemplified by the group consisting of NO, CO, $CO_2$, and ammonia (E. Flory, *Fed. Proc.*, 26, 1164–1176 (1967)), steroids and steroid hormones (C. L. Coascogne et al., *Science*, 237, 1212–1215 (1987)), adenosine and other purines, and prostaglandins.

e. Neuromediators

Neuromediators can be exemplified by the group consisting of cyclic AMP, cyclic GMP (F. E. Bloom, *Rev. Physiol. Biochem. Pharmacol.*, 74, 1–103 (1975), and cyclic nucleotide-dependent protein phosphorylation reactions (P. Greengard, *Distinguished Lecture Series of the Society of General Physiologists*, 1, Raven Press: New York (1978)).

f. Sedative-Hypnotics

Sedative-hypnotics can be exemplified by the group consisting of benzodiazepines and buspirone, barbiturates, and miscellaneous sedative-hypnotics. A. J. Trevor and W. L. Way, "Sedative-Hypnotics" in *Basic and Clinical Pharmacology*; B. G. Katzung, Ed.; Appleton and Lange; Chapter 21, pp. 306–319 (1992).

g. Antiepileptic Neurologically Active Compounds

Suitable antiepileptic drags can be exemplified by the groups consisting of, but not limited to, hydantoins such as phenytoin, mephenytoin, and ethotoin; anticonvulsant barbiturates such as phenobarbital and mephobarbital; deoxybarbiturates such as primidone; iminostilbenes such as carbamazepine; succinimides such as ethosuximide, methsuximide, and phensuximide; valproic acid; oxazolidinediones such as trimethadione and paramethadione; benzodiazepines and other antiepileptic agents such as phenacemide, acetazolamide, and progabide. See T. W. Rail et al., "Drugs Effective in the Therapy of the Epilepsies", in *The Pharmacological Basis of Therapeutics, 8th Edition;* A.

G. Gilman et al., Eds.; Pergamon Press: New York; Chapter 19, pp. 436–462 (1990).

h. Parkinsonism and other Movement Disorders

Neurologically active compounds that are effective in the treatment of Parkinsonism and other movement disorders include, but are not limited to, dopamine, levodopa, carbidopa, amantadine, baclofen, diazepam, dantrolene, dopaminergic agonists such as apomorphine, ergolines such as bromocriptine, pergolide, and lisuride, and anticholinergic drugs such as benztropine mesylate, trihexyphenidyl hydrochloride, procyclidine hydrochloride, biperiden hydrochloride, ethopropazine hydrochloride, and diphenhydramine hydrochloride. See J. M. Cedarbaum et al., "Drugs for Parkinson's Disease, Spasticity, and Acute Muscle Spasms", in *The Pharmacological Basis of Therapeutics, 8th Edition;* A. G. Gilman et al., Eds.; Pergamon Press: New York; Chapter 20, pp. 463–484 (1990).

i. Opioid Analgesics and Antagonists

Suitable opioid analgesics and antagonists can be exemplified by the group consisting of, but not limited to, endogenous opioid peptides such as enkephalins, endorphins, and dynorphins; morphine and related opioids such as levorphanol and congeners; meperidine and congeners such as piperidine, phenylpiperidine, diphenoxylate, loperamide, and fentanyl; methadone and congeners such as methadone and propoxyphene; pentazocine; nalbuphine; butorphanol; buprenorphine; meptazinol; opioid antagonists such as naloxone hydrochloride; and centrally active antitussive agents such as dextromethorphan. See J. H. Jaffe et al., "Opioid Analgesics and Antagonists" in *The Pharmacological Basis of Therapeutics, 8th Edition;* A. G. Gilman et al., Eds.; Pergamon Press: New York; Chapter 21, pp. 485–521 (1990).

j. Antipsychotic Compounds

Neurologically active compounds that can be used to treat depression, anxiety or psychosis are also useful in the present invention. Suitable antipsychotic compounds include, but are not limited to, phenothiazines, thioxanthenes, dibenzodiazepines, butyrophenones, diphenylbutylpiperidines, indolones, and rauwolfia alkaloids. Mood alteration drugs that are suitable for use in the present invention include, but are not limited to, tricyclic antidepressants (which include tertiary amines and secondary amines), atypical antidepressants, and monoamine oxidase inhibitors. Examples of suitable drugs that are used in the treatment of anxiety include, but are not limited to, benzodiazepines. R. J. Baldessarini, "Drugs and the Treatment of Psychiatric Disorders", in *The Pharmacological Basis of Therapeutics, 8th Edition;* A. G. Gilman et al., Eds.; Pergamon Press: New York; Chapter 18, pp. 383–435 (1990).

3. Neuroactive Proteins

The neurologically active compound useful in the present conjugate may also be a neuroactive protein, such as human and chimeric mouse/human monoclonal antibodies, erythropoietin and G-CSF, orthoclone OKT3, interferongamma, interleukin-1 receptors, t-PA (tissue-type plasminogen activator), recombinant streptokinase, superoxide dismutase, catalase, glutathione peroxidase, tissue factor pathway inhibitor (TFPI). See *Therapeutic Proteins: Pharmacokinetics and Pharmacodynamics;* A. H. C. Kung et al., Eds.; W. H. Freeman: New York, pp 1–349 (1993).

4. Neuroactive Nonprotein Drugs

The neurologically active compound useful in the present conjugate may also be a neuroactive nonprotein drug, such as free radical scavengers, neurotransmitter receptors and pharmacological targets in Alzheimer's disease; Design and Synthesis of BMY21502: A Potential Memory and Cognition Enhancing Agent; muscarinic agonists for the central nervous system; serotonic receptors, agents, and actions; thiazole-containing 5-hydroxytryptamine-3 receptor antagonists; acidic amino acids as probes of glutamate receptors and transporters; L-2-(carboxycyclopropyl)glycines; and N-Methyl-D-aspartic acid receptor antagonists. See *Drug Design for Neuroscience;* A. P. Kozikowski, Ed.; Raven Press: New York, pp 1–469 (1993).

5. Approved Biotechnology Drugs or Biotechnology Drugs in Development

The neurologically active compound useful in the present conjugate may also be an approved biotechnology drug or a biotechnology drug in development. Exemplary members of this group are included on Tables 1 and 2 (approved biotechnology drugs and biotechnology drugs in development, respectively) and may be found in J. E. Talmadge, *Advanced Drug Delivery. Reviews,* 10, 247–299 (1993).

TABLE 1

Approved Biotechnology Drugs

| Approved Drugs Product Type | Abbreviated Indication | Date Approved |
|---|---|---|
| Interferon-gamma 1b | Chronic granulomatous disease | Dec. 1990 |
| Interferon-alpha-n | Genital warts | Oct. 1989 |
| Epoetin-alpha | Anemia of chronic renal failure | Dec. 1990 |
| Epoetin-alpha | Anemia of chronic renal failure | Dec. 1990 |
| Interferon-alpha-2b | Hairy cell leukemia | June 1986 |
|  | Genital warts | June 1986 |
|  | AIDS-related Kaposi's sarcoma | Nov. 1988 |
|  | Non-A and non-B hepatitis | Feb. 1991 |
| Sargramostin (CSF-GM) | Autologous bone marrow transplant | March 1991 |
| Sargramostin (CSF-GM) | Autologous bone marrow transplant | March 1991 |
| Filgrastim (r-CSF-G) | Chemotherapy-induced neutropenia | Feb. 1991 |
| Interferon-alpha-2a | Hairy cell leukemia | June 1986 |
|  | AIDS-related Kaposi's sarcoma | Nov. 1988 |
| Aldesleukin (IL-2) | Renal cell carcinoma | May 1992 |

TABLE 2

Biotechnology Drugs in Development

| Approved Drugs Product Type | Abbreviated Indication | U.S. Status |
|---|---|---|
| Colony-stimulating factors | | |
| CSF-GM | Adjuvant to chemotherapy | Phase I/II |
| CSF-GM | Low blood cell counts | Submitted |
| sargramostim (CSF-GM) | Allogeneic bone marrow transplants, chemotherapy adjuvant | Phase II |
| | Adjuvant to AIDS therapy | Phase II |
| CSF-M | Cancer, fungal disease | Phase I |
| CSF-M | Cancer, hematologic neoplasms, bone marrow transplants | Phase I |
| Filgrastim (r-CSF-G) | AIDS, leukemia aplastic anemia | Submitted |
| Sargramostim (CSF-GM) | Neutropenia to secondary chemotherapy | Phase III |
| Erythroproietins | | |
| Epoetin-beta | Anemia secondary to kidney disease | Submitted |
| | Autologous transfusion | Phase II/III |
| Epoetin-alpha | Anemia of cancer and chemotherapy | Submitted |
| | Anemia of surgical blood loss. autologous transfusion | Phase III |
| Interferons | | |
| Interferon-gamma-1b | Small-cell lung cancer, atop dermatitis | Phase III |
| | Trauma-related infections, renal cell carcinoma | Phase II |
| | Asthma and allergies | Phase I |
| Interferon-alpha-n3 | ARC, AIDS | Phase I/II |
| Interferon-beta | Multiple sclerosis | Phase III |
| | Cancer | Phase I/II |
| Interferon-gamma | Rheumatoid arthritis | Phase II/III |
| | Venereal warts | Phase II |
| Interferon consensus | Cancer, infectious disease | Phase III |
| Interferon-gamma | Cancer, infectious disease | Phase II |
| Interferon-alpha-2b | Superficial bladder cancer, basal cell carcinoma, chronic hepatitis B, delta hepatitis | Submitted |
| | Acute hepatitis B, delta hepatitis, acute chronic myelogenous leukemia | Phase III |
| | HIV (with Retrovir) | Phase I |
| Interferon-beta | Unresponsive malignant disease | Phase I |
| Interferon-alpha-2a | colorectal cancer (with 5-fluorouracil); chronic, acute hepatitis B; non-A, non-B hepatitis, chronic myelogenous leukemia; HIV positive, ARC, AIDS (with Retrovir) | Phase II |
| Interleukins | | |
| PEG-IL-2 | AIDS (with Retrovir) | Phase I |
| Aldesleukin (IL-2) | Cancer | Phase II/III |
| | Kaposi's sarcoma (with Retrovir) | Phase I |
| Human IL-1 alpha | Bone marrow suppression (chemo/radiotherapy) | Phase I/II |
| Human IL-1 beta | Bone marrow suppression, melanoma, immunotherapy | Phase I/II |
| | Wound healing | Phase II |
| Human IL-2 | Cancer immunotherapy | Phase II |
| Human IL-2 | Cancer immunotherapy (with Roferon-A) | Phase II |
| Human IL-3 | Bone marrow failure, platelet deficiencies, autologous marrow transplant, chemotherapy adjuvant | Phase I/II |
| Human IL-4 | Immunodeficient disease, cancer therapy, vaccine adjuvant immunization | Phase I/II |
| Human IL-4 | Cancer immunomodulator | Phase II |
| Human IL-6 | Platelet deficiencies | Phase I |
| Tumor necrosis factors | | |
| TNF | Cancer | Phase II |
| TNF | Cancer | Phase II |
| Others | | |
| Anakinra (IL-1 receptor antagonist) | AML, CML, inflammatory, rheumatoid arthritis, sepsis, septic | Phase II |

TABLE 2-continued

Biotechnology Drugs in Development

| Approved Drugs Product Type | Abbreviated Indication | U.S. Status |
|---|---|---|
| Disaccharide tripeptide glycerol | shock | |
| Dipalmitoyl (macrophage activator) | Metastatic colorectal cancer to the liver | Phase II |
| Monophosphoryl lipid A | Gram-negative septic shock | Phase I |
| MTP PE | Osteogenic sarcoma | Phase III |

6. Neurotrophic Proteins

A preferred group of neurologically active compounds for use in the present conjugate is a group of proteins that are generally referred to as neurotrophic proteins. These include nerve growth factor itself (NGF), brain-derived neurotrophic factor (BDNF), neurotrophin-3 (NT-3), neurotrophin-4 (NT-4), neurotrophin-5 (NT-5), insulin-like growth factors (IGF-I and IGF-II), glial cell line derived neurotrophic factor (GDNF), fibroblast growth factor (FGF), ciliary neurotrophic factor (CNTF), epidermal growth factor (EGF), glia-derived nexin (GDN), transforming growth factor (TGF-$\alpha$ and TGF-$\beta$), interleukin, platelet-derived growth factor (PDGF) and S100l$\beta$ protein, as well as bioactive derivatives and analogues thereof (such as PNT-1). Representative classes of this class are listed on Table 3, below.

TABLE 3

Neurotrophic Proteins

| Neurotrophic Proteins | References |
|---|---|
| Neuronal Growth Factor (NGF) | Johnson et al., Neurochem. Res., 12, 985–994 (1987); Meakin et al., Trends Neurosci., 15, 323–331 (1992): Koliatsos et al., Ann. Neurol., 30, 831–840 (1991); Hefti et al., Neurobiol. Aging, 10, 515–533 (1989); and Williams et al., Proc. Natl. Acad. Sci. USA, 83, 9231–92,)5 (1986) |
| Brain-Derived Neurotrophic Factor (BDNF) | Koliatsos et al., Neuron, 359–367 (1993); Yan et al., Nature, 360, 753–755 (1992); Hyman et al., Nature, 350, 230–233 (1991); Sendtner et al., Nature, 360, 757–759 (1992); Knüsel et al., J. Neurosci., 12, 4391–4402 (1992); and Hohn et al., Nature, 344, 339–341 (1990) |
| Neurotrophin-3 | Maisonpierre et al., Science, 247, 1446–1451 (1990); Lohof et al., Nature, 360, 350–353 (1993); Kalcheim et al., Proc. Natl. Acad. Sci, USA, 89, 1661–1665 (1992); Dechant et al., J. Neurosci, 13, 2610–2616 (1993); Callazo et al.. Neuron. 9, 643–646 (1992); Wong et al., Eur. J. Neurosci., 5, 466–474 (1993); Ip et al., Neuron, 10, 137–149 (1993) |
| Neurotrophin-4 | Ibanez et al., Development, 117, 1345–1353 (1993); Ip et al., Proc. Natl. Acad. Sci. USA, 89, 3060–3064 (1992); Wong et al., Eur. J. Neurosci, 5, 466–474 (1993); and Ip et al., Neuron, 10, 137–149 (1993) |
| Neurotrophin-5 | Berkemeier et al., Neuron, 7, 857–866 (1991); Wong et al., Eur. J. Neurosci., 5, 466–474 (1993); and Ip et al., Neuron, 10, 137–149 (1993) |
| Insulin-like Growth Factors: Insulin-like Growth Factor I (IGF-I), and Insulin-like Growth Factor II (IGF-II) | Fernyhough et al., Brain Res., 607, 117–124 (1993); Araujo et al., Brain Res., 484, 130–138 (1999); Near et al., Proc. Natl. Acad. Sci. USA, 89, 11716–11720 (1992); Gluckman et al., Biochem. Biophys. Res. Commun., 182, 593–599 (1992); Carson et al., Neuron, 10, 729–740 (1993); and Baskin et al., Trends Neurosci., 11, 107–111 (1988) |
| Glial Cell-Line Derived Neurotrophic Factor (GDNF) | Lin et al., Science, 260, 1130–1132 (1993); Henderson et al.. Science, 266, 1062–1064 (1994); Tomac et al., Nature, 373, 335–339 (1995); Beck et al., Nature, 373, 339–341 (1995); Yan et al., Nature, 373, 341–344 (1995); and Oppenheim et al., Nature, 373, 344–346 (1995) |
| Fibroblast Growth Factor (a-FGF, b-FGF) | Sasacki et al., Neurochem, Int., 21, 397–402 (1992); Cummings et al., Brain Res., 591, 271–276 (1992); Wanaka et al., Neuron, 5, 267–281 (1990); Unsicker et al., Ann, N.Y. Acad. Sci., 638, 300–305 (1991); and Enokido et al., Brain Res., 599, 261–271 (1992) |
| Ciliary Neurotrophic Factor (CNTF) | Clatterbuck et al., Proc. Natl. Acad. Sci. USA, 90, 2222–2226 (1993); Louis et al., Science, 259, 689–692 (1993); Apfel et al., Brain Res., 604, 1–6 (1993); Ip et al., J. Physiol-Paris, 85, 123–130 (1993); and Ip et al., Eur. J. Neurosci., 5, 25–33 (1993: |
| Epidermal Growth Factor | Hefti et al., Neurobiology of Aging, 10, 5125 (1989); |

TABLE 3-continued

Neurotrophic Proteins

| Neurotrophic Proteins | References |
| --- | --- |
| (EGF) | Morrison, J. Neurosci. Res., 17, 99 (1987): Morrison et al., J. Neuromi. Res., 21, 71 (1988); Fallon et al., Science, 224, 1107 (1984); Gomex-Pinilla, Brain Res., 438, 385 (1988); and Lakshmanan et al., J. Neurochem., 46, 1081 (1986) |
| Glia-derived Nexin (GDN) | Guenther et al., EMBO J., 4, 1963 (1985); Sommer et al., Biochemistry, 26, 6407 (1987); Gloor et al., Cell, 47, 687 (1986); Rosenblatt et al., Brain Res., 415, 40 (1987); and Reinhard et al., Neuron, 1, 387 (1988) |
| Transforming Growth Factor (TGF-α, TGF-β) | Derynck, Cell, 54, 593 (1988); Wilcox et al., J. Neurosci., 8., 1901 (1988) |
| Interleukins (Interleukin-1, Interleukin-2) | Geulian et al., Science, 228, 497 (1985); Neito-Sampedro, J. Neurosci. Res., 17, 214 (1987); Lindholm et al., Nature, 230, 658 (1987); Neito-Sampedro et al., Neurochem. Res., 12, 723 (1987); and Benveniste et al., Neuroimmunol., 17, 301 (1988) |
| Platelett-derived Growth Factor (PDGF) | Mellstrom et al., J. Muscle Res. Cell Motil., 4, 589 (1983) |
| Pan-neurotrophin 1 (PNT01) | Ilag et al., Proc. Natl. Acad, Sci. USA, 92, 607–611 (1995) |
| S100β Protein | Kligman et al., PNAS USA, 82, 7136 (1985) |

7. Antioxidants and Other Free Radical Scavengers

Another preferred group of neurologically active compounds for use in the present invention is a group of compounds generally referred to as antioxidants or free radical scavengers. Oxygen radicals play a critical role in the development of many neurological disorders, including post-traumatic and post-ischemic neuronal degeneration, chronic neurodegenerative diseases such as familial amyotrophic lateral sclerosis (FALS) and Parkinson's disease (PD), and aging. See, for example, Warner, "Superoxide dismutase, aging, and degenerative disease", *Free Radical Biol. Med.*, 17, 249 (1994). The reactive oxygen species, primarily superoxide, is generated by the one electron reduction of molecular oxygen. Halliwell et al., "Oxygen toxicity, oxygen radicals, transition metals and disease", *Biochem. J.*, 219, 1 (1984). This superoxide anion radical ($O_2^-$) and its protonated forms, perhydroxyl radical ($HO_2$), hydrogen peroxide ($H_2O_2$), and hydroxyl radical ($OH^-$), are chemically unstable, highly reactive, and can attack and modify all classes of cellular elements, including lipids, proteins, and nucleic acids, thereby causing tissue injury and cell death.

During the pathogenesis of the aforementioned neurological disorders, the endogenous superoxide eliminating system, superoxide dismutase (SOD), is unable to reduce the massive superoxide production. Thus, the delivery of antioxidants, such as superoxide dismutase, catalase, glutathione peroxide, and the like, will limit the neuronal damage caused by free radicals in these neurological disorders.

B. Carrier molecules

Carrier molecules which can be used in accord with the present invention include any molecule which can be conjugated or cross-linked to the neurologically active compound so that the ability of the neurologically active compound to cross the BNB or BBB is "substantially enhanced" over the nonconjugated form of the neurologically active compound. The term "substantially enhanced" or "enhanced" is to be understood in the context of the increases in the permeability across the BNB or the BBB observed for conjugated neurologically active compounds over that observed for the nonconjugated forms, i.e., an at least about 5-20-fold increase measured by the methodologies disclosed herein.

The increase in permeability of the blood-brain or blood-nerve barrier in response to the carrier molecule relates not only to the quantity of molecules passing from the blood to the brain, but also, to the type of molecule of interest. The effect of the carrier molecule is to preferentially increase the passage of small or large molecular weight substances through the blood-brain or blood-nerve barrier. The term "increases in the permeability across the BNB or BBB" refers to that observed for conjugated neurologically active compounds over that observed for the non-conjugated forms. The term "effective amount" as used herein means that amount of the carrier molecule which will significantly increase the blood-brain barrier permeability for the neurologically active compound of interest. In other words, it will increase the permeability at the blood-brain barrier to allow sufficient quantifies of the neuroactive compound of interest to pass from the blood to the interstitial fluid of the brain or nerve to exert a therapeutic or prophylactic effect or allow diagnostic procedures. The effective amount will be determined on an individual basis and will be based, at least in part, on consideration of the individual's size, age, the specific state or disease to be treated, the severity of the symptoms to be treated, the result sought, the specific carrier molecule used, and other variations among hosts, etc. Thus, the effective amount can be determined by one of ordinary skill in the art employing such factors and using no more than routine experimentation.

Only modest levels of success have been observed in treatment of neurological disorders with neurologically active compounds, most likely because of the extremely short half-life of some compounds as well as the fact that, even though exhibiting high permeabilities relative to other compounds, that these neurologically active compounds have difficulty passing the BBB or BNB. As described hereinabove, efficient delivery across the BBB and BNB is critical to a therapeutic strategy in treating neurological disease. Thus, peptides and proteins with high permeabilities to the BNB or BBB are preferably used as carrier molecules for the delivery of neurologically active compounds in the treatment of neurological diseases. Additionally, it is advantageous that carrier molecules be of low molecular weight for the delivery of neurologically active compounds as is described in the present invention. It is important, however, that the bioactivity of the neurologically active compounds be substantially preserved after modification or coupling to a carrier molecule. Also, the neurologically active compounds must be delivered to a discrete population of affected neurons or glia within the nervous system.

Thus, carrier molecules that are indicated for use in the present invention are those with high permeability coefficient-surface area product (PS) values, i.e., values that exceed $5 \times 10^{-6}$ ml/g/s and that are at least 5–20-fold higher than that of the native neurologically active compound, are useful. While it might be preferred to use carrier molecules that have the highest PS values as carriers of neurologically active compounds, carrier molecules that have PS values in the lower range may be useful clinically because of the characteristics of the individual proteins or low molecular weight compounds.

1. Polyamines

Covalent attachment of polyamines dramatically increases the permeability of the neurologically active compounds of the present invention at both the BBB and the BNB. Useful polyamines include synthetic and naturally occurring polyamines of empirical formula $C_xH_yN_z$, which may comprise cyclic or acyclic branched or unbranched —$CH_2$— chains of 3–12 carbon atoms, further comprising 1–6 NR or N(R)$_2$ moieties, wherein each R is H, ($C_1$–$C_4$) alkyl, phenyl or benzyl. Preferably, the polyamine comprises 1-4NH or NH$_2$ moieties in the polyamine. Preferably, the polyamines are naturally occurring and include putrescine, spermidine, spermine, 1,3-diaminopropane, norspermidine, syn-homospermidine, thermine, thermospermine, caldopentamine, homocaldopentamine and canavalmine. See, for example, T. Oshima et al., *J. Biol, Chem.*, 257, 9913 (1982); T. Oshima et al., *J. Biochem.*, 93, 1455 (1983) and S. Fujihara et al., *Biochem. Biophys. Res. Comm.*, 107, 403 (1982). Endogenous polyamines, including putrescine (PUT), spermidine (SPD), and spermine (SPM), are preferred for use in the present method. These compounds are ubiquitously present in all cells and have long been known to play roles in proliferation and differentiation of many cell types. Tabor "Polyamines", *Annu. Rev. Biochem.*, 53,749 (1984). Naturally occurring polyamines, such as PUT, SPD, SPM, are normal cell metabolites and can be covalently attached to proteins as has been described in liver, kidney, testis, in aplysia neurons, and in numerous cultured cells, including human peripheral lymphocytes, chinese hamster ovary (CHO) cells, mouse epidermal cells, and murine neuroblastoma. Furthermore, although proof of the occurrence of covalent polyamine-protein conjugates has been demonstrated in many cells, little information is available as to the biological significance of these covalent reactions.

Two pathways for post-translational modifications of proteins involving the natural polyamines have been described. The first involves the formation of hypusine [N$^\epsilon$(4-amino-2-hydroxybutyl)lysine], in which the butylamine residue derived from spermidine is covalently linked to the ε- amino group of lysine residues of proteins and then hydroxylated. The second pathway involves polyamines that are in covalent amide-linkage to the γ-carboxyl groups of protein glutamic acid residues, a reaction catalyzed by transglutaminases that are widely distributed in mammalian cells and fluids. Folk et al., "Polyamines as physiological substrates for transglutaminases", *J. Biol. Chem.*, 255, 3695 (1980).

It is well known that the endothelial cell surface bears a negative surface charge at physiological pH because of sulfated mucopolysaccharides, proteoglycans, sialic acid containing glycoproteins and glycolipids, sulfated glycoproteins and glycolipids, carboxyl groups of proteins, and phosphates of proteins and phospholipids. This electrostatic barrier repels negatively charged molecules. For this reason, it is known among those of skill in the art that the injection of cationic molecules results in an increase in the permeability of cerebral vessels. Friedemann et al., "The Blood-Brain Barrier in Infectious Diseases—It's Permeability to Toxins in Relation to their Electrical Charges", *Lancet*, 226, 719 (1934). Polycationic protamine sulfate, cationized ferritin, poly-L-lysine, and sulfated dextrans have all been shown to increase the permeability of horseradish peroxidase in rat brain. Nagy et al., "Endothelial Surface Charge: Blood-Brain Barrier Opening to Horseradish Peroxidase Induced by Polycation Protamine Sulfate", *Acta Neuropathol.*, 7, 7 (1981). However, the precise mechanism by which cationic molecules affect the permeability of the BBB or BNB after binding to the anionic sites on the endothelial cell surface is not known.

The covalent attachment of naturally-occurring polyamines may play a role in allowing charge interactions of the polyamine-modified proteins with the negative surface charge of membranes, and thus, it may be hypothesized that this charge interaction may increase the permeability of such cationic proteins by facilitating absorptive endocytosis. However, the experimental examples provided herein below demonstrate the surprising discovery that increasing the charge valency on proteins with different naturally occurring polyamines resulted in a significant decrease in the permeability. This finding demonstrates that the observed permeability changes that are the basis of the present invention occur by a mechanism other than simple electrostatic interaction.

C. Polyamine Linkage to Neurologically Active Compounds

There are many approaches for the chemical cross-linking or "linkage" of neurologically active compounds to carrier molecules, whether they be other peptides, proteins or other low molecular weight compounds. Significant advancement in the application of these cross-linking agents has led to the synthesis of cleavable bifunctional compounds. There are over 300 cross-linkers now available, and it is clear to one of skill in the art that multiple approaches can be used to chemically cross-link neurologically active compounds to carrier molecules. In the method of the present invention, the linkage of a neurologically active compound to one of the above-mentioned carrier molecules can be accomplished in a manner so that the ability of the carrier molecule to bind to its receptor is not significantly altered, nor is the bioactivity of the neurologically active compound significantly affected by the cross-linking procedure.

Numerous considerations, such as reactivity, specificity, spacer arm length, membrane permeability, cleavability and solubility characteristics need to be evaluated when choosing an appropriate cross-linker. A recent review of the "Chemistry of Protein Conjugation and Cross-Linking" can be found by Shan S. Wong, CRC Press, Ann Arbor, 1991. The most important question, perhaps, is what functional groups are available for coupling. These functional groups must not be involved in the binding to the receptor or the inactivation of the therapeutic agent. For example, if only lysines or N-terminal amino acids are available, a logical choice would be NHS-ester homobifunctional cross-linkers. If one molecule has lysines and the other sulfhydryls, a maleimide NHS-ester cross-linker would be an appropriate choice. If only lysines are available on both molecules, modification to introduce sulfhydryls via the lysines on one molecule would allow for sequential coupling. If both molecules have free sulfhydryls, a homobifunctional sulfhydryl reactive cross-linker would be appropriate. If carboxyls and amines are available, carbodiimide works well. Furthermore, if there are no readily reactive groups, a photoactivatible cross-linker can be used. If lysines are important for the functionality of the molecule, then a cross-linker that will couple through sulfhydryls, carboxyls, or nonspecifically can be used.

To preserve the receptor binding capacity of the carrier molecule, as well as its bioactivity, it may be necessary to choose an appropriate spacer arm length between a cross-linker and the carrier molecule. Similarly, if solubility is a problem and organic solvents are detrimental to the carrier molecule or neurologically active compound, then there are many commercially available water soluble cross-linkers, such as the sulfonated NHS-ester homo- and heterobifunctional cross-linkers.

Linking reagents have at least two reactive groups and can be either homobifunctional with two identical reactive groups or heterobifunctional with two or more different reactive groups. Trifunctional groups also exist and can contain three functional groups. Most homobifunctional cross-linkers react with primary amines commonly found on proteins. Other homobifunctional cross-linkers couple through primary sulfhydryls. Homobifunctional cross-linkers can be used in a one step reaction procedure in which the compounds to be coupled are mixed and the cross-linker is added to the solution. The resulting cross-linking method may result in self-conjugation, intermolecular cross-linking, and/or polymerization. The following are examples of suggested cross-linking approaches and are not meant to be inclusive.

Imido esters are the most specific acylating reagents for reaction with the amine groups whereby in mild alkaline pH, imido esters react only with primary amines to form imidoamides. The product carries a positive charge at physiological pH, as does the primary amine it replaces and therefore, does not affect the overall charge of the protein.

Homobifunctional N-hydroxysuccinimidyl ester conjugation is also a useful cross-link approach to crosslink amine-containing proteins. Homobifunctional sulfhydryl reactive cross-linkers include bismaleimidhexane (BMH), 1,5-difluoro-2,4-dinitrobenzene (DFDNB), and 1,4-di-(3',2'-pyridyldithio) propionamido butane (DPDPB).

Many heterobifunctional cross-linkers are commercially available with the majority containing an amine-reactive functional group on one end and a sulfhydryl-reactive group on the other end. Multiple heterobifunctional haloacetyl cross-linkers are available, as are pyridyl disulfide cross-linkers. In addition, heterobifunctional cross-linking reagents which react with carboxylic groups involves the carbodiimides as a classic example for coupling carboxyls to amines resulting in an amide bond.

D. Dosage Forms/Modes of Administration

The invention also provides pharmaceutical compositions suitable for administration to animals to increase the permeability of the BBB or BNB to a neurologically active compound of interest. Furthermore, the method of the present invention may also employ a pharmaceutically acceptable carrier in which the conjugate would be administered. Such compositions will comprise an effective amount of the conjugate in combination with a pharmaceutically acceptable carrier. The pharmaceutically acceptable carrier may be a liquid, so that the composition is adapted for parenteral administration, or may be solid, i.e., a capsule shell plus vehicle, a tablet, a pill and the like, formulated for oral administration. Furthermore, the pharmaceutically acceptable carrier may be in the form of a nebulizable liquid or solid so that the composition is adapted for inhalation. When administered parenterally, the composition should be pyrogen free and in an acceptable parenterally acceptable carrier having due regard for pH, isotonicity, and stability. Dosage formulations of the conjugate of the present invention are prepared for storage or administration by mixing the compound having the desired degree of purity with physiologically acceptable excipients or stabilizers.

If the pharmaceutically acceptable carrier is a solid formulated for oral administration adjuvants may be incorporated. Typical adjuvants which may be incorporated into tablets, capsules and the like are binders, excipients, disintegrating agents, lubricants, sweetening agents and flavoring agents. When the dosage form is a soft gelatin capsule, in addition to the above materials, it may also contain a liquid carrier such as a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as water or a naturally occurring vegetable oil like sesame, peanut, or cottonseed oil or a synthetic fatty vehicle like ethyl oleate or the like may be desired. Buffers preservatives, antioxidants and the like can be incorporated according to accepted pharmaceutical practice.

Sustained release compositions also include liposomally entrapped conjugates. Liposomes containing the conjugate are prepared by known methods. See Epstein et al., *PNAS USA*, 82, 3688 (1985) and Hwang et al, *PNAS USA*, 77, 4030 (1980). Ordinarily the liposomes are of the small (about 200–800 angstroms) unilamellar type in which the lipid content is greater than about 30 mol. % cholesterol, the selected proportion being adjusted for the optimal neurologically active compound therapy.

The dosage to be administered will be determined by the attending physician taking into account various factors known to modify the action of drugs. These include severity and type of disease, body weight, sex, diet, time and route of administration, other medications and other relevant clinical factors. Typically, the daily regime will range from about 1–3000 µg/kg body weight. Preferably the dosage will range from about 10–1000 µg/kg body weight. Most preferably, the dosage will range from about 0.01–150 mg/day. Therapeutically effective dosages may be determined by either in vitro or in vivo methods.

The invention will be further described by reference to the following detailed examples.

Animals and Reagents. Male Sprague-Dawley rats (24-weeks-old, 460–500 g) were obtained from Bio Lab (St. Paul) and were used to determine the PS and $V_p$ measurements. All animals were kept for a minimum of 3 days under standard housing conditions and feeding schedules prior to the experiments. SOD, isolated from bovine erythrocytes with a monomeric molecular weight of 16,250 daltons, was obtained from Worthington Biochemical Corporation (Freehold, N.J.). The dimer contains two Cu (II) and two Zn (II) atoms per molecule. Ultrapure 2.55 NGF was obtained from Harlan Bioproducts (Madison, Wis.). Insulin ($M_r$ = 6000) was obtained as humulin RU-100 from Eli Lily.

Human albumin ($M_r$=67,000) was isolated from normal human plasma by using CM-Affi-Gel Blue (Bio-Rad) and further subjected to boronate affinity chromotography to remove the glycated species. Affinity purified human IgG was obtained from Accurate Chemicals ($M_r$=150,000). Carrier-free sodium $^{125}$I and sodium $^{131}$I were obtained from Amersham. Protein concentrations were determined by the BCA protein assay procedure of Smith et al. (*Anal. Biochem.*, 150, 76–85 (1985)) using the Pierce Assay Kit with BSA as the standard. Plasma half-lives were determined from plasma clearance curves for all the proteins using the standard exponential decay equation in In Plot Scientific Graphics (Graph Pad Software).

determined from the plasma clearance curves (Table 4, below). PUT-INS has a plasma half-life that was 1.7 fold less than that of the native insulin; SPD-ALB had a plasma half-life that was approximately 12 fold less than the native albumin; and PUT-IgG had a plasma half-life that was approximately 30 fold less than that of the native protein. This data shows that polyamine modification of different proteins, with varying $M_r$ and function, dramatically decreased their circulating plasma half-life.

TABLE 4

Plasma Half-Life for INS/PUT-INS, ALB/SPD-ALB, and IgG/PUT-IgG

|  | INS | PUT-INS | ALB | SPD-ALB | IgG | PUT-IgG |
|---|---|---|---|---|---|---|
| $t_{1/2}$ (min) | 1.18 ± 0.09 | 0.70 ± 0.02 | 10.42 ± 1.40 | 0.87 ± 0.03 | 30.20 ± 5.85 | 0.99 ± 0.10 |
| P |  | <0.000 1 |  | 0.0002 |  | 0.0076 |

$\bar{x}$ ± SEM
n = 5
P: two tailed test

EXAMPLE 1

Polyamine Modification of Neurologically Active Compounds a. NGF

NGF was modified with putrescine at carboxylic acid groups using the water-soluble carbodiimide. 0.4M putrescine in deionized, distilled water was adjusted to a pH of 6.7, followed by the addition of 3 mg of NGF and 0.2 g of the water-soluble 1-ethyl-3-[3-dimethylaminopropyl]-carbodiimide hydrochloride. The reaction mixture was stirred for four hours at room temperature and maintained at pH 6.7. The sample was then dialyzed with multiple changes of deionized, distilled water over a seven day period and froze at –70° C. until used. The bioactivity of the modified NGF was evaluated for neurite outgrowth on DRG and PC12 culture systems. No discernible difference was observed with the PUT-NGF compared to native protein.

b. Superoxide Dismutase (SOD), Insulin (INS), Albumin (ALB) and IgG.

Carboxylic acid groups on SOD, INS, ALB, and IgG were activated to the reactive ester with water-soluble carbodiimide and then reacted with polyamines as nucleophilic reagents. The following reaction scheme was generally used: 0.4M polyamine (putrescine (PUT), spermidine (SPD), or spermine (SPM)) in deionized, distilled water was adjusted to pH 4.7 with HCl followed by the addition of 1 mg protein (SOD, INS, ALB or IgG). 0.2 g of the water-soluble 1-ethyl-3-[3-dimethylaminopropyl]-carbodiimide hydrochloride was then added. The reaction mixture was stirred for four hours at room temperature and maintained at a constant pH of 4.7. The sample was then dialyzed with multiple changes of deionized, distilled water over a seven day period. The product was then lyophilized and stored at –4° C. for subsequent radioiodination.

Polyamine modification of INS, ALB, and IgG resulted in dramatic decreases in the half-lives of the proteins as As can be seen in Table 5, below, there was a highly significant decrease in the plasma half-lives with all three polyamines after SOD modification compared to native SOD. This decrease ranged from 4.9-fold less for SPD-SOD to 5.7-fold less for SPM-SOD.

TABLE 5

Plasma Half-Life for SOD and PSOD

|  | SOD | PUT-SOD | SPD-SOD | SPM-SOD |
|---|---|---|---|---|
| $t_{1/2}$ (min) | 3.64 ± 0.21 | 0.66 ± 0.03 | 0.75 ± 0.05 | 0.64 ± 0.06 |

$\bar{x}$ ± SEM
n = 6 c. Polyamine Modification of Superoxide Dismutase (SOD) at Variable pH

Carboxylic acid groups of superoxide dismutase (SOD) were activated to the reactive ester with water-soluble carbodiimide and then reacted with putrescine as the nucleophilic reagent. Briefly, 0.4M putrescine in distilled, deionized water was adjusted to a pH of between 4.7 and 7.7 (specifically, pH's of 4.7, 5.7, 6.7 and 7.7) with HCL followed by the addition of 1 mg SOD. The water soluble 1 ethyl-3-[3-dimethylaminopropyl]-carbodiimide hydrochloride (0.2 g) was then added. This reaction was then stirred for four hours at room temperature and maintained at a constant pH. Following dialysis with multiple changes of deionized, distilled water over a seven day period, the product was lyophilized and stored at –20° C. for subsequent radioiodination.

The enzyme activity for SOD and PUT-SOD modified at variable pH was determined using a spectrophotometric assay for superoxide dismutase activity. This assay was purchased as a kit (SOD-525) from Bioxytech, Cedex, France. Data is expressed as a percentage of the native unmodified enzyme.

As shown in FIG. 1, there is a corresponding decrease in the activity of SOD after modification with PUT as the pH of the reaction is decreased. Interestingly, modification at pH 7.7 resulted in a percent activity that was higher than the native enzyme (108.71±0.26% of native SOD). With decreasing pH, a corresponding decrease in the activity of the enzyme was observed reaching a value of 6.6±2.87% of native SOD at pH 4.7. Also shown in FIG. 1, are the PS values for PUT-SOD for the endoneurium and hippocampus after modification at different pH. The PS values were lowest at pH 7.7 and highest at pH 4.7 with values for the endoneurium at 47.18±2.10×10$^{-6}$ ml/g/sec and 43.35±3.81× 10$^{-6}$ ml/g/sec for the hippocampus. Additional modifications of SOD were performed at the intermediate pH of 6.2 and 6.0. PS values at pH 6.0 were 21.30±4.80×10$^{-6}$ ml/g/sec for the endoneurium and 20.10±0.42×10$^{-6}$ ml/g/sec for the hippocampus with corresponding enzyme activity of 55.64±1.14% of native SOD. From these studies, it is apparent that an increased PS value for the PUT-SOD resulted in a corresponding decrease in the enzyme activity.

This experiment demonstrates that the preservation of SOD enzyme activity after covalent attachment of polyamines can be realized by limiting the ionization of the protein carboxylic acid groups during the modification with carbodiimide, and further that an increased PS value for PUT-SOD results in a corresponding decrease in enzyme activity. This experiment further indicates that with a target PS value of 20×10$^{-6}$ ml/g/s (or, alternatively, at least 10-fold higher than that of the native protein), greater than 50% enzyme activity will be retained. As indicated in FIG. 1, this would be accomplished by limiting the pH of the modification with polyamines to a range of 5.7–6.0.

EXAMPLE 2

Radioiodination of Neurologically Active Compounds and Conjugates

Aliquots of the neurologically active compounds as well as the neurologically active compounds conjugated to polyamines ("conjugates") were labeled with $^{125}$I and $^{131}$I using the chloramine-T method as described previously by Poduslo et al., *Proc. Natl. Acad Sci. USA*, 85, 4879 (1988). Free radioactive iodine was separated from the radiolabeled conjugates and agents by dialysis against 0.2M NaI. Purity of the radiolabeled conjugates and agents were determined by paper chromatography as described by Poduslo et al., *J. Neurosci.*, 2, 1507 (1982). The radiolabeled conjugates and agents that stayed at the origin were always greater than 99% of the total radioactivity. The radioiodinated conjugates and agents were evaluated by SDS-PGE or SDS-PAGE as previously described by Poduslo, *Anal. Biochem.*, 114, 131 (1981). No degradative products were found after iodination or after PS/$V_p$ measurements were made.

EXAMPLE 3

SDS-PAGE and IEF analyses

Polyamine modified proteins were evaluated by SDS polyacrylamide gel electrophoresis with a gel concentration of 15% T and 1% C using a Tris-glycine buffer system as described by Poduslo in "Glycoprotein molecular weight estimation using SDS-pore gradient electrophoresis: comparison of TRIS-glycine and TRIS-borate-EDTA buffer systems", *Anal. Biochem.*, 114, 131 (1981). Protein samples were solubilized in SDS under reducing conditions with 2-mercaptoethanol followed by electrophoresis and staining with Coomassie blue. Pharmacia low molecular weight calibration kit was used for the protein standards. The 40% Bio-Lyte 3/10 ampholyte from Bio-Rad was used for isoelectric focusing with an acrylamide monomer concentration of 25% T and 3% C. Polymerization time was 15 minutes, with 5 minutes allowed for sample diffusion. Electrophoresis time was 45 minutes with increasing voltage to a maximum voltage of 450 volts for the last 15 minutes. IEF standards were obtained from Bio-Rad and contained nine natural proteins with the isoelectic points ranging from 4.45 to 9.6 and were visualized with Coomassie blue.

a. NGF

Figure 2:
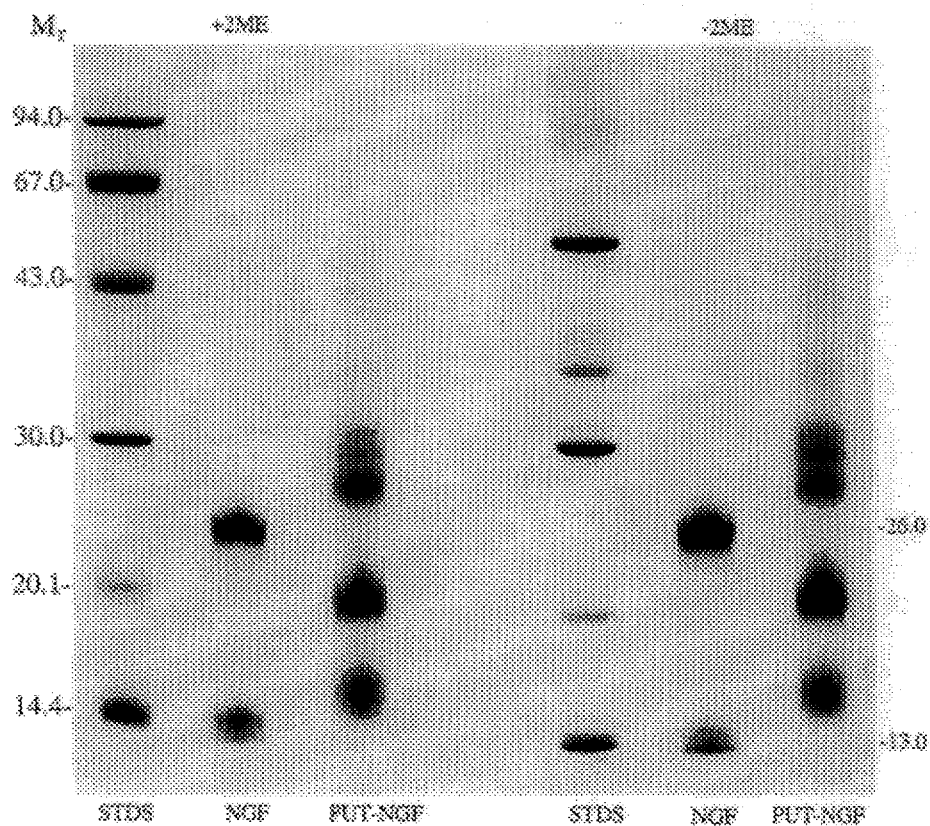
FIG. 2 is a photograph of the SDS-PAGE analysis of NGF and PUT-NGF.

SDS-PAGE analysis of NGF and PUT-NGF under reducing and non-reducing conditions can be seen in FIG. 2. The 2.5 S NGF exists as a dimer with a molecular weight of 26,000 and a non-covalently attached monomer of 13,000. After polyamine modification, higher apparent molecular weight species are observed with no differences in electrophoretic mobilities under reducing or non-reducing conditions.

Figure 3:
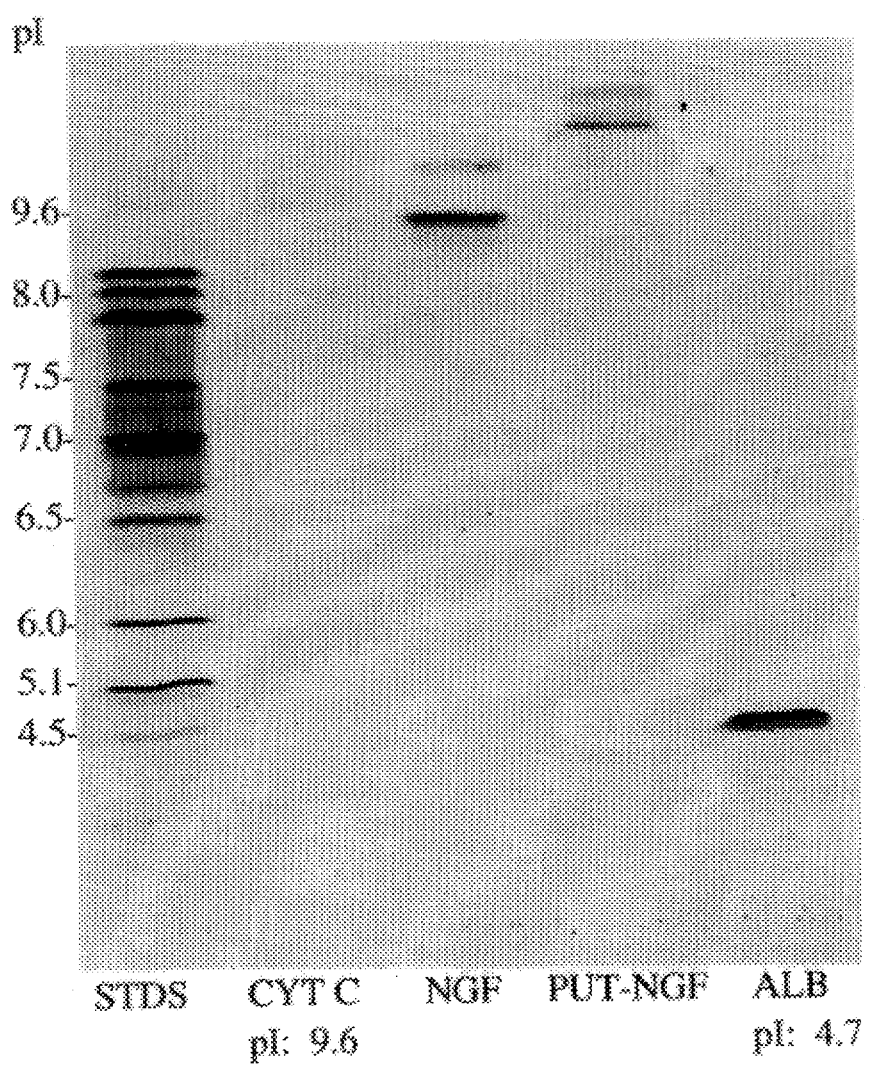
FIG. 3 is a photograph of isoelectric focusing after Coomassie Blue stain, showing a shift in pI of NGF after modification with PUT.

These studies demonstrate that under the reaction conditions, all the NGF was modified with putrescine and, hence, further separation of the modified and non-modified protein was not necessary. By isoelectric focusing after Coomassie blue stain (FIG. 3), native NGF revealed a major band with an isoelectric point less than cytochrome c and a minor species with isoelectric point greater than cytochrome c. After modification with putrescine, a shift to a higher pI was observed. No residual modified NGF was observed, which again indicates that no further chromatographic separation was necessary to separate NGF from the modified NGF.

b. SOD

1. SOD Modified with PUT at Variable pH

Figure 4:
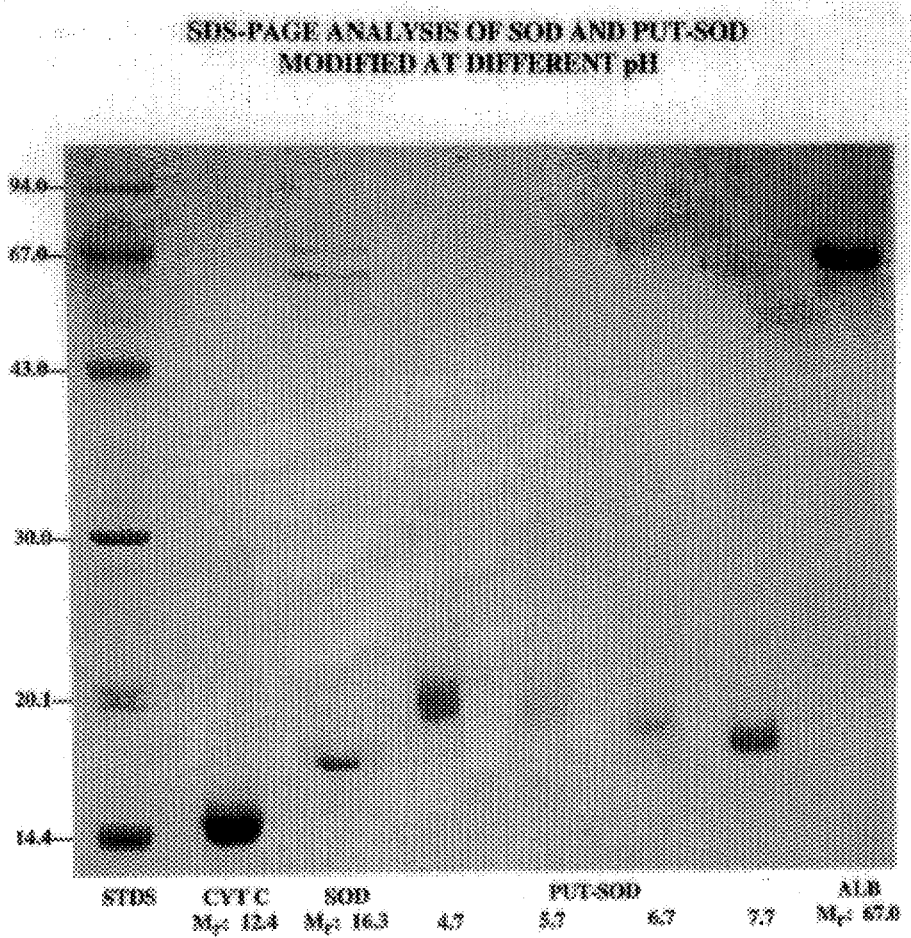
FIG. 4 is a photograph of the SDS-PAGE analysis of SOD and PUT-SOD.
Figure 5:
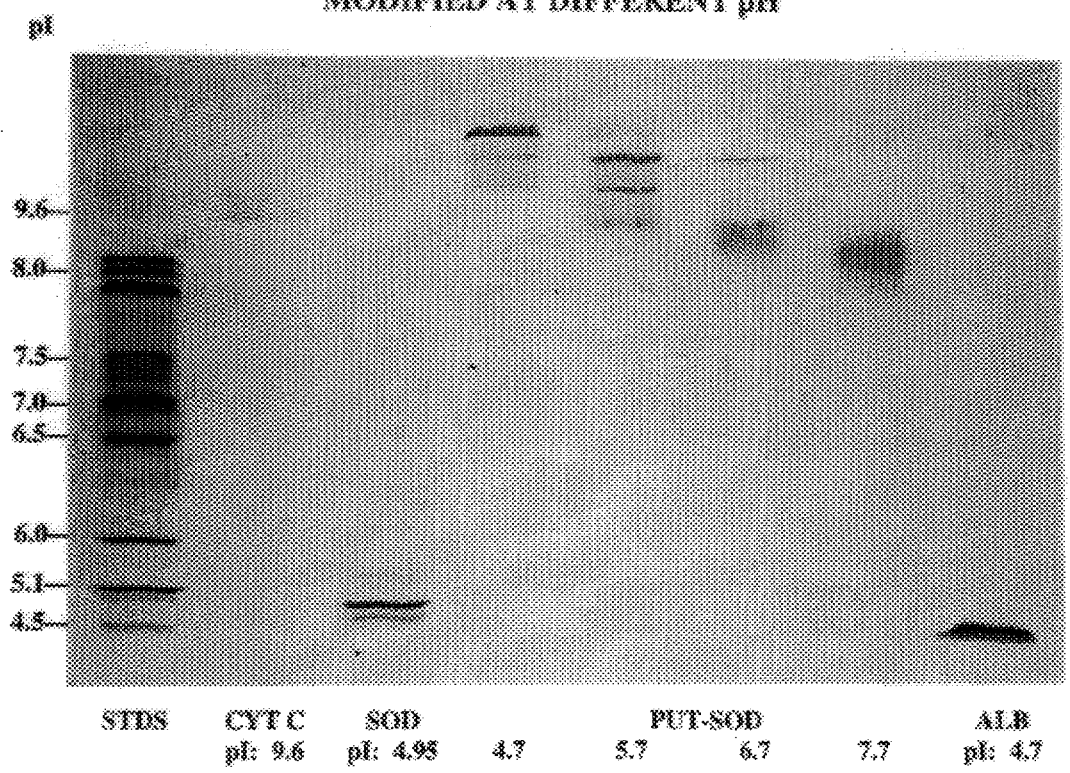
FIG. 5 is a photograph of the results of isoelectric focusing after Coomassie Blue stain, showing a shift in pI of SOD after modification with PUT.

SOD was modified with PUT at pH 4.7, 5.7, 6.7, and 7.7 as described above. SDS-PAGE revealed a graded increase in molecular weight at each pH for the modified SOD compared to the native SOD (FIG. 4). Under the reaction conditions at each pH, all the SOD was modified with PUT and, hence, further separation of the modified and unmodified protein was not necessary. This graded molecular weight shift demonstrates that increasing numbers of carboxylic acid groups on SOD were activated with decreasing pH. Furthermore, no high molecular weight aggregates of PUT-SOD were observed. As determined by isoelectric focusing after Coomassie blue stain, native SOD has a pI of 4.95 with several species (FIG. 5). Modification of SOD with putrescine at the different pH resulted in a complete shift to increasing basic isoelectric points that were of the order pH 4.7>5.7>6.7>7.7. Reaction at these different pH values clearly demonstrates different degrees of polyamine modification of the carboxylic acid groups. No residual unmodified SOD was observed at any pH indicating again that no further chromatographic separation was necessary to separate the native SOD from the polyamine-modified SOD. These experiments demonstrate that SOD can be readily modified with PUT and the degree of the modification is controlled by the pH of the reaction.

2. SOD Modified with Spermine, Spermidine and Putrescine at pH 4.7

Figure 6:
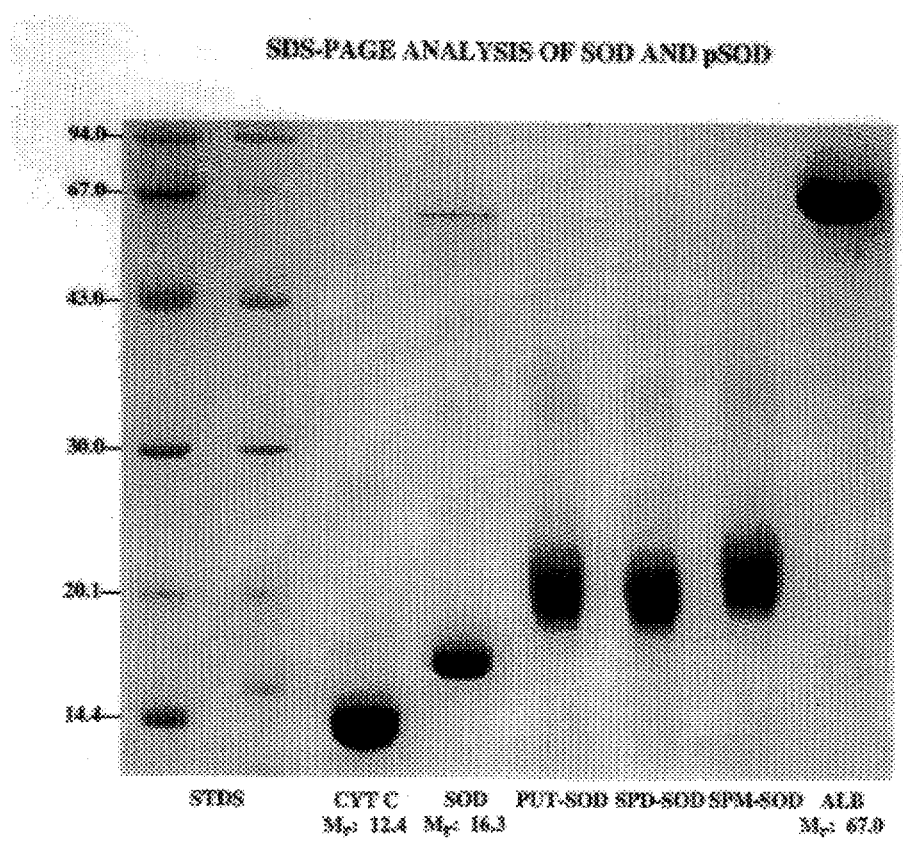
FIG. 6 is a photograph of the SDS-PAGE analysis of SOD and SOD modified with putrescine (PUT), spermine (SPM) and spermidine (SPD).
Figure 7:
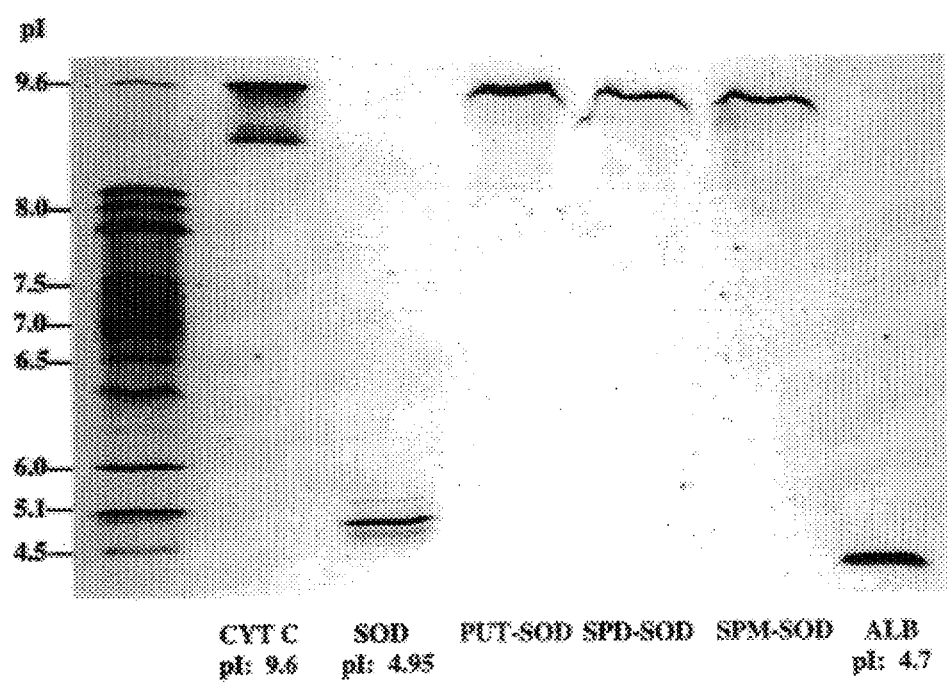
FIG. 7 is a photograph of the results of isoelectric focusing after Coomassie Blue stain, showing a shift in pI of SOD after modification with PUT, SPM and SPD.

The extent of modification of SOD by polyamines was examined using two different electrophoretic techniques. The monomeric subunit of SOD has a molecular weight of 16,250 daltons as observed after Coomassie blue staining of the polyacrylamide gel, and after modification with the three different polyamines, a shift to a higher molecular weight is observed (approximately 20,000 daltons) (FIG. 6). Modification with all three polyamines showed a similar shift to the higher molecular weight. Under our reaction conditions, all of the SOD was modified with polyamine and, hence, further separation of the modified and unmodified protein was not necessary. By isoelectric focusing after Coomassie Blue stain, native SOD has a pI of 4.95 with several species (FIG. 7). After modification with the three different polyamines, the pI of SOD shifted to a value similar to that of cytochrome c (pI=9.6). All three polyamines showed a similar pI as defined by the acrylamide monomer concentration with no residual unmodified SOD in the preparation (FIG. 7). Again, no further chromatographic separation was necessary to separate the native SOD from the modified SOD. These experiments demonstrate that SOD is readily modified with polyamines and that the protein becomes basic as a result of the accumulation of positive charges contributed by the polyamines.

EXAMPLE 4

Choline acetyltransferase (CHAT) assay of NGF and PUT-NGF

Cells of the basal forebrain, in particular the medial septal nuclei, are strongly cholinergic and appear to play principle roles in learning and memory. Substantial experimental evidence suggest that NGF regulates ChAT as well as acetylcholine production in these neurons. More recently, NGF has been shown to induce NOS (mRNA, protein and activity) in these neurons, which further suggests that NGF influences basal forebrain function by regulating the production of NO as well as acetylcholine.

Most neurons of the nucleus basalis are cholinergic with about 90% of them projecting to widespread regions in the cerebral cortex. The nucleus basalis is often thought to be the major source of cholinergic innervation of the entire cerebral cortex. The nucleus basalis is particularly relevant to Alzheimer's disease because neurons in this nucleus are selectively degenerated in this disease and in its variant, senile dementia of the Alzheimer's type which occurs in middle and late life. This well-documented cortical cholinergic deficiency that occurs in these patients is characterized by the loss of cholinergic input from neurons in the nucleus basalis. Pathologically, there is diffuse degeneration of the cerebral cortex involving all layers, senile amyloid plaques in the cortex, intraneuronal fibrillary tangles, and selective degeneration of the cells in the nucleus basalis. This experiment was conducted to determine whether there would be a significant increase in ChAT activity in cells of these brain regions when treated with PUT-NGF compared to native NGF, after parenteral administration in the normal adult animal where the BBB is not compromised.

a. NGF Administration

Adult BALB/cJ mice were used. The injection site was alternated on a daily basis between I.M. (thigh) and I.V. injection (tail vein), and the vehicle consisted of 1.5 mg/ml of BSA in 0.9% NaCl. The amount of NGF or PUT-NGF injected was 15 µg/day/animal for a duration of 14 days. Three groups of animals (n=7) were injected with either vehicle alone, NGF, and PUT-NGF. At the end of the experiment, the brains were removed and dissected into five regions which included the septum, hippocampus, nucleus basalis (substantia innominata), caudate-putamen (neostriatum), and cortex and stored at −70° C. The septum was dissected from the hippocampus at the fornix and continued into the basal forebrain.

Subsequently, a radiochemical assay using [1-$^{14}$C] acetyl-CoA was performed according to the method of Fonnum. Fonnum, "A rapid radiochemical method for the determination of choline acetyltransferase", *J. Neurochem.*, 24, 407 (1975). Data were expressed as cpm/µg protein and are given as mean ± SEM. Protein concentration was determined by the BCA procedure (Smith et al., "Measurement of protein using bicinchoninic acid", *Anal. Biochem.*, 150, 76 (1985)) with the Pierce assay kit using bovine serum albumin as a standard. Statistical analysis was by the unpaired t-test (two-tailed) with significance accepted as $P<0.05$.

As shown in Table 6, below, there was no significant difference between the vehicle and NGF treatment groups for ChAT activity in the five different brain regions. In contrast, a highly significant difference was observed with the PUT-NGF treatment versus NGF alone for the septum and nucleus basalis. A highly significant 48.5% increase in ChAT activity was observed in the septum (P=0.024) and a 69.7% increase was observed in the nucleus basalis (P=0.039) after treatment with PUT-NGF compared to native protein. No changes were observed in ChAT activity in the hippocampus, caudate-putamen, or cortex after treatment with the modified NGF compared to the native protein.

TABLE 6

ChAT Activity in Different Brain Regions After Parenteral Administration of Vehicle, NGF, and PUT-NGF

| | | | NGF vs. Vehicle | | | PUT-NGF vs. NGF | |
|---|---|---|---|---|---|---|---|
| | Vehicle | NGF | % Increase | P | PUT-NGF | % Increase | P |
| Septum | 442 ± 40 | 443 ± 65 | 0.2 | NS | 658 ± 45 | 48.5 | 0.024 |
| Hippocampus | 235 ± 4 | 236 ± 17 | 0.4 | NS | 236 ± 10 | 0 | NS |
| Nucleus Basalis | 97 ± 8 | 109 ± 15 | 12.4 | NS | 185 ± 30 | 69.7 | 0.039 |
| Caudate-Putamen | 472 ± 10 | 559 ± 47 | 18.4 | NS | 541 ± 24 | −0.3 | NS |
| Cortex | 281 ± 8 | 294 ± 9 | 4.6 | NS | 314 ± 9 | 6.8 | NS |

ChAT Activity: cpm/µg protein; $\bar{x}$ ± SEM
P: unpaired t-test (two-tailed)
NS: not significant (P>0.05)
n = 7 animals per group This experiment demonstrates that there is a significant increase in ChAT activity in cells of the septum when treated with PUT-NGF systemically delivered to the normal adult animals over a period of two weeks compared to native NGF. In addition to these alterations in ChAT activity in the septum, an even more pronounced effect was observed in the nucleus basalis. Furthermore, this experiment demonstrates not only enhanced permeability of polyamine-modified NGF compared to native NGF, but that the protein is still biologically active and is targeted to specific brain regions populated by cholinergic neurons where a response is elicited in these neurons as determined by an increase in ChAT activity. Since these studies were performed in normal adult animals where the blood-brain barrier has not been compromised, this experiment also provides evidence that the delivery of a neurotrophic protein across the intact BBB elicits a bioresponse in specific brain regions after peripheral systemic administration.

EXAMPLE 5

Administration of Radioiodinated Conjugates and Neurologically Active Agents The experimental protocol employed was based on the methods of Ohno et al. *Am. J. Physiol.*, 235, H299–H307 (1978) and Rapoport et al., *Brain Res.*, 172, 354–359 (1979) with modifications as described by Poduslo et al., *PNAS USA*, 89, 2218–2222 (1992). Briefly, the I.V. bolus injection technique was used whereby a bolus of phosphate buffered saline containing the $^{125}$I-unconjugated neurologically active agents and $^{125}$I-conjugates was rapidly injected into the catheterized brachial vein of pentobarbitol-anesthetized rats. Over the next 30 or 60 minutes, serial blood samples were collected from the brachial artery to generate a plasma washout curve. At times of 15, 30 or 60 seconds prior to the end of the experiment, the second isotope-labeled conjugate or neurologically active agent ($^{125}$I) was administered I.V. to serve as the $V_p$ indicator.

After the final blood sample was collected, the animal was sacrificed, the brain and meninges removed, and the brain dissected into the cortex, caudateputamen (neostriatum), hippocampus, thalamus, brain stem, and cerebellum. The sciatic nerve was also rapidly removed and desheathed. Tissue was lyophilized, and dry weights were determined with a microbalance and converted to respective wet weights with wet weight/dry weight ratios previously determined for the deshseathed rat sciatic nerve and the various brain regions. Both tissue and plasma samples were assayed for $^{125}$I and $^{131}$I radioactivity in a two-channel gamma counter with the radioactivity corrected for cross-over of $^{131}$I activity into the $^{125}$I channel and background. $V_p$ and PS measurements were calculated as described by Poduslo et al., *Proc. Natl. Acad. Sci. USA*, 89, 2218 (1992). Statistical evaluations were performed using the t-test with significance accepted at the P<0.05 level.

1. PS and $V_p$ Measurements of Radioiodinated Neurologically Active Compounds a. NGF Table 7, below, shows the PS and $V_p$ measurements at the BNB for NGF and PUT-NGF. PUT-NGF, when modified at pH 6.7, had a PS of 10.83×10$^{-6}$ ml/g/sec, which was a significant 6.2-fold greater than the native protein. Modification of NGF at this pH does not affect the bioactivity of NGF as determined by neurite outgrowth on PC12 and DRG culture systems. While modification at lower pH can dramatically increase the permeability at both the BNB and BBB, bioactivity is correspondingly affected. No difference was observed in the residual plasma volume ($V_p$) in these experiments.

TABLE 7

PS and $V_p$ of the BNB for NGF and PUT-NGF

|  | NGF | PUT-NGF | PUT-NGF vs. NGF | |
|---|---|---|---|---|
|  |  |  | RI | P |
| PS: ml/g/sec × 10$^6$ | 1.74 ± 0.15 | 10.83 ± 0.95 | 6.2 | <0.0001 |
| $V_p$: µl/g | 1.53 ± 0.12 | 1.81 ± 0.13 | 1.2 | NS | x̄ ± SEM; n = 10
P: unpaired t-test (two-tailed)
NS: not significant (P>0.05)

Table 8 identifies the PS and $V_p$ of the BBB for NGF and PUT-NGF. PS values of PUT-NGF range from 9.31–15.1× 10$^{-6}$ ml/g/sec for the different brain regions, which represented a relative increase that range from 4.4–6.2-fold greater than the native NGF. No significant differences were observed in the $V_p$ values between the modified and native NGF.

TABLE 8

PS and $V_p$ of the BNB for NGF and PUT-NGF

|  | NGF | PUT-NGF | PUT-NGF vs. NGF | |
|---|---|---|---|---|
|  |  |  | RI | P |
| PS: ml/g/sec × 10$^6$ |  |  |  |  |
| Cortex | 1.91 ± 0.07 | 9.31 ± 0.97 | 4.9 | <0.0001 |
| Caudate-putamen | 1.64 ± 0.04 | 10.21 ± 1.21 | 6.2 | 0.0001 |
| Hippocampus | 2.30 ± 0.10 | 10.82 ± 0.82 | 4.7 | <0.0001 |
| Thalamus | 2.79 ± 0.09 | 13.21 ± 1.19 | 4.7 | <0.0001 |
| Brain Stem | 3.38 ± 0.09 | 15.10 ± 1.41 | 4.4 | <0.0001 |
| Cerebellum | 2.93 ± 0.10 | 14.58 ± 1.01 | 5.0 | <0.0001 |
| $V_p$: µl/g |  |  |  |  |
| Cortex | 7.19 ± 0.20 | 6.36 ± 0.48 | 0.9 | NS |
| Caudate-putamen | 5.78 ± 0.42 | 6.43 ± 0.20 | 1.1 | NS |
| Hippocampus | 8.56 ± 0.21 | 7.39 ± 0.87 | 0.9 | NS |
| Thalamus | 11.65 ± 0.81 | 11.35 ± 1.27 | 1.0 | NS |
| Brain Stem | 16.60 ± 1.01 | 15.21 ± 2.08 | 0.9 | NS |
| Cerebellum | 11.54 ± 0.71 | 11.14 ± 1.23 | 1.0 | NS | x̄ ± SEM; n = 5
P: unpaired t-test (two-tailed)
NS: not significant (P>0.05)

These experiments demonstrate that polyamine modification of NGF can enhance permeability of this protein across the BNB and BBB without affecting the bioactivity of the protein.

b. INS/PUT-INS, ALB/SPD-ALB, and IgG/PUT-IgG

The PS and $V_p$ values of the BNB and BBB for INS and PUT-INS are seen in Tables 9 and 10, below. Native insulin had a PS value in nerve of 33.2×10$^{-6}$ ml/g/sec and values that ranged from 15.8 to 22.6×10$^{-6}$ ml/g/sec for the different brain regions. Modification of INS with putrescine resulted in a significant increase in the PS values that ranged from a 1.7 to 2.0 fold increase for both the BNB and BBB. In general, no significant differences were observed in the $V_p$ values after putrescine modification; the cortex and thalamus did have significant $V_p$ values. A decrease in the time of administration of the second isotope, however, resulted in nonsignificant differences in the $V_p$ values for these brain regions.

TABLE 9

PS and $V_p$ of the BNB for INS and PUT-INS

|  | INS | PUT-INS | PUT-INS vs. INS | |
|---|---|---|---|---|
|  |  |  | RI | P |
| PS: ml/g/sec × $10^6$ | 33.19 ± 2.05 | 65.06 ± 2.75 | 2.0 | <0.0001 |
| $V_p$: μl/g | 5.05 ± 0.87 | 5.13 ± 0.73 | 1.0 | NS |

$\bar{x}$ ± SEM
n = 10
P: two-tailed t-test
NS: not significant (P>0.05)

TABLE 10

PS and $V_p$ of the BNB for INS and PUT-INS

|  | INS | PUT-INS | PUT-INS vs. INS | |
|---|---|---|---|---|
|  |  |  | RI | P |
| PS: ml/g/sec × $10^6$ | | | | |
| Cortex | 15.78 ± 2.45 | 27.94 ± 1.09 | 1.8 | 0.004 |
| Caudate-putamen | 16.88 ± 1.79 | 28.52 ± 2.63 | 1.7 | 0.013 |
| Hippocampus | 17.16 ± 2.55 | 29.68 ± 1.35 | 1.7 | 0.004 |
| Thalamus | 18.42 ± 2.41 | 34.84 ± 1.11 | 1.9 | 0.001 |
| Brain Stem | 22.62 ± 3.35 | 38.13 ± 1.43 | 1.7 | 0.006 |
| Cerebellum | 20.12 ± 2.78 | 38.48 ± 1.23 | 1.9 | 0.001 |
| $V_p$: μl/g | | | | |
| Cortex | 6.44 ± 0.49 | 10.16 ± 1.10 | 1.6 | 0.024 |
| Caudate-putamen | 6.08 ± 0.30 | 9.79 ± 1.15 | 1.6 | NS |
| Hippocampus | 7.04 ± 0.68 | 9.57 ± 1.14 | 1.4 | NS |
| Thalamus | 7.60 ± 0.67 | 12.24 ± 1.16 | 1.6 | 0.022 |
| Brain Stem | 12.35 ± 0.99 | 15.76 ± 1.61 | 1.3 | NS |
| Cerebellum | 10.56 ± 0.96 | 18.72 ± 3.06 | 1.8 | NS |

$\bar{x}$ ± SEM
n = 5
P: two-tailed t-test
NS: not significant (P>0.05)

The PS and $V_p$ values of the BNB and BBB for ALB and SPD-ALB are shown in Tables 11 and 12, below. SPD-modified ALB showed a PS value of 31.3×$10^{-6}$ ml/g/sec in nerve. This is 165 fold greater than that of the native protein with no corresponding change in the $V_p$ values. In addition, PS values for SPD-ALB were 54–136 fold greater than that of the native albumin in the six different brain regions, with no corresponding change in the residual plasma volume.

TABLE 11

PS and $V_p$ of the BNB for ALB and SPD-ALB vs ALB

|  | ALB | SPD-ALB | SPD-ALB vs ALB | |
|---|---|---|---|---|
|  |  |  | RI | P |
| PS: ml/g/sec × $10^6$ | 0.19 ± 0.03 | 31.32 ± 5.43 | 164.8 | 0.0001 |
| $V_p$: μl/g | 1.86 ± 0.12 | 3.15 ± 0.72 | 1.7 | NS |

$\bar{x}$ ± SEM
n = 12
P: two-tailed t-test
NS: not significant (P>0.05)

TABLE 12

PS and $V_p$ of the BNB for ALB and SPD-ALB

|  | ALB | SPD-ALB | SPD-ALB vs ALB | |
|---|---|---|---|---|
|  |  |  | RI | P |
| PS: ml/g/sec × $10^6$ | | | | |
| Cortex | 0.18 ± 0.04 | 13.01 ± 1.96 | 72.3 | 0.0013 |
| Caudate-putamen | 0.11 ± 0.02 | 14.94 ± 1.89 | 135.8 | 0.0005 |
| Hippocampus | 0.20 ± 0.02 | 14.87 ± 2.17 | 74.4 | 0.0011 |
| Thalamus | 0.23 ± 0.03 | 17.08 ± 1.94 | 74.3 | 0.0003 |
| Brain Stem | 0.43 ± 0.03 | 23.07 ± 2.94 | 53.7 | 0.0006 |
| Cerebellum | 0.39 ± 0.06 | 21.80 ± 2.83 | 55.9 | 0.0006 |
| $V_p$: μl/g | | | | |
| Cortex | 4.85 ± 0.59 | 6.09 ± 1.34 | 1.3 | NS |
| Caudate-putamen | 4.99 ± 0.49 | 7.11 ± 1.46 | 1.4 | NS |
| Hippocampus | 6.23 ± 0.30 | 6.44 ± 1.39 | 1.0 | NS |
| Thalamus | 8.02 ± 0.39 | 9.24 ± 1.95 | 1.2 | NS |
| Brain Stem | 10.83 ± 0.63 | 13.94 ± 3.03 | 1.3 | NS |
| Cerebellum | 11.94 ± 0.94 | 12.40 ± 1.92 | 1.0 | NS |

$\bar{x}$ ± SEM
n = 6
P: two-tailed t-test
NS: not significant (P>0.05)

Similar relationships were found with IgG after polyamine modification. Tables 13 and 14, below, indicate the increases in the PS of the BNB and BBB for PUT-IgG compared to native IgG. A 349 fold increase was observed in PS for the BNB of PUT-IgG compared to native IgG, with no significant difference in the corresponding $V_p$ values. Similarly, the relative increase in PS values of the BBB for PUT-IgG ranged from 111 to 313 fold for the different brain regions with no significant difference in the corresponding $V_p$ values.

TABLE 13

PS and $V_p$ of the BNB for IgG and PUT-IgG vs IgG

|  | IgG | PUT-IgG | PUT-IgG vs IgG | |
|---|---|---|---|---|
|  |  |  | RI | P |
| PS: ml/g/sec × $10^6$ | 0.08 ± 0.01 | 27.93 ± 1.23 | 349.1 | <0.0001 |
| $V_p$: μl/g | 1.84 ± 0.14 | 4.64 ± 0.76 | 2.5 | NS |

$\bar{x}$ ± SEM
IgG: n = 10
PUT-IgG: n = 14
P: two-tailed t-test
NS: not significant (P>0.05)

TABLE 14

PS and $V_p$ of the BBB for IgG and PUT-IgG

|  | IgG | PUT-IgG | PUT-IgG vs IgG | |
|---|---|---|---|---|
|  |  |  | RI | P |
| PS: ml/g/sec × $10^6$ | | | | |
| Cortex | 0.05 ± 0.01 | 7.82 ± 0.48 | 156.4 | <0.0001 |
| Caudate-putamen | 0.03 ± 0.01 | 9.40 ± 0.66 | 313.3 | <0.0001 |

TABLE 14-continued

PS and $V_p$ of the BBB for
IgG and PUT-IgG

|  | IgG | PUT-IgG | PUT-IgG vs IgG | |
|---|---|---|---|---|
|  |  |  | RI | P |
| Hippocampus | 0.04 ± 0.01 | 9.00 ± 0.58 | 225.0 | <0.0001 |
| Thalamus | 0.06 ± 0.01 | 9.85 ± 0.71 | 164.2 | <0.0001 |
| Brain Stem | 0.10 ± 0.02 | 11.12 ± 1.22 | 111.2 | <0.0001 |
| Cerebellum | 0.09 ± 0.02 | 10.92 ± 0.77 | 121.3 | <0.0001 |
| $V_p$: µl/g |  |  |  |  |
| Cortex | 3.93 ± 0.21 | 5.25 ± 0.72 | 1.3 | NS |
| Caudate-putamen | 4.18 ± 0.20 | 6.15 ± 0.84 | 1.5 | NS |
| Hippocampus | 4.44 ± 0.22 | 5.50 ± 0.63 | 1.2 | NS |
| Thalamus | 5.78 ± 0.24 | 7.25 ± 1.06 | 1.3 | NS |
| Brain Stem | 7.20 ± 0.71 | 10.56 ± 1.71 | 1.5 | NS |
| Cerebellum | 7.54 ± 0.59 | 8.51 ± 1.00 | 1.1 | NS | x̄ ± SEM
IgG: n = 5
PUT-IgG: n = 7
P: two-tailed t-test
NS: not significant (P>0.05)

These experiments demonstrate that polyamine modification of NGF, INS, ALB, IgG and SOD (see later) can dramatically increase the permeability of these proteins across the BNB and BBB compared to the native proteins. Since these proteins differ widely with regard to molecular weight and function, it is probable that this methodology can be extended to other neurologically active compounds than those described or in the example.

c. SOD (1) Modified at pH 4.7

The PS and $V_p$ values of the BNB and BBB for SOD and pSOD (polyamine-modified SOD) are seen in Tables 15 and 16, below. Native SOD had a PS value of the BNB of $2.24 \times 10^{-6}$ ml/g/sec (Table 15) which is approximately 22 fold greater than the PS value obtained from native albumin. Poduslo et al., "Macromolecular permeability across the blood-nerve and blood brain barriers", *Proc. Natl. Acad. Sci. USA*, 91, 5705 (1994). Modification of SOD with putrescine resulted in a PS value of $47.18 \times 10^{-6}$ ml/g/sec which represents a 21.1-fold increase compared to the native SOD.

The PS for SPD-SOD was significantly less with a value of $24.1 \times 10^{-6}$ ml/g/sec, which is still 10.8 fold greater than native SOD. SPM-SOD was also significantly less than SPD-SOD with a value of $13.85 \times 10^{-6}$ ml/g/sec or 6.2 fold greater than native SOD. The $V_p$ values for SPD-SOD and SPM-SOD were not significantly different from that of the native SOD (Table 15). The $V_p$ for PUT-SOD reached significance which was 1.8-fold greater than the $V_p$ value for native SOD. These values were obtained by the administration of the second isotope at 30 seconds prior to the end of the experiment which is near the plasma half-life of PUT-SOD (Table 5). This indicates that some transport of the $^{125}$I-PUT-SOD is consequently occurring during this 30 second interval. When the second isotope was administered at 15 seconds prior to the end of the experiment, no significant differences were observed for the $V_p$ values for PUT-SOD.

TABLE 15

PS and $V_p$ of the BNB for SOD and pSOD

| SOD | PUT-SOD | PUT-SOD vs SOD | | SPD-SOD SPD-SOD | | | SPM-SOD vs SOD | |
|---|---|---|---|---|---|---|---|---|
| (n = 12) | (n = 12) | RI | P | (n = 12) | RI | P | (n = 10) | RI | P |
| Ps: ml/g/sec × 10⁶ |  |  |  |  |  |  |  |  |  |
| 2.24 ± 0.22 | 47.18 ± 2.10 | 21.1 | <0.001 | 24.1 ± 1.23 | 10.8 | <0.001 | 13.85 ± 1.16 | 6.2 | <0.001 |
| $V_p$: µl/g |  |  |  |  |  |  |  |  |  |
| 2.63 ± 0.22 | 4.82 ± 0.60 | 1.8 | <0.05 | 3.03 ± 0.35 | 1.2 | NS | 2.57 ± 0.15 | 1.0 | NS | x̄ ± SEM
P: ANOVA
NS: not significant (P>0.05)

Six different brain regions were evaluated for the PS and $V_p$ values of the BBB for SOD and SOD modified with putrescine, spermidine, and spermine (Table 16). Native SOD had PS values that ranged from approximately $1.8 \times 10^{-6}$ ml/g/sec for the cortex and caudate-putamen to a high of $3.13 \times 10^{-6}$ ml/g/sec for the brain stem. This represented a relative increase in the PS for SOD of 12 fold for the cortex to 54 fold for the brain stem compared to native albumin. Putrescine-modified SOD showed the largest increase in the PS with values that ranged from $34.75 \times 10^{-6}$ ml/g/sec for the cortex to a high of $56.65 \times 10^{-6}$ ml/g/sec for the brain stem. This represented a relative increase of 17.6 to 23.6 fold of the PUT-SOD compared to native SOD. The PS values for SPD-SOD for the different brain regions were less than that for the PUT-SOD and ranged from 25 to $37.3 \times 10^{-6}$ ml/g/sec, which represented a relative increase from 11.8 to 18.3 fold greater than the native SOD. SPM-SOD had PS values that ranged from 6.8 to $12.3 \times 10^{-6}$ ml/g/sec for the different brain regions with a relative increase of 3.7–4.2 fold. Significance was reached with the thalamus, brain stem, and cerebellum. The residual plasma volume ($V_p$) for the different brain regions for the polyamine-modified SODs are also found in Table 16. The $V_p$ values for SPM-SOD and SPD-SOD were not significantly different from those of the native protein. The $V_p$ of PUT-SOD just reached significance in the different brain regions reflecting that some of the $^{131}$I-PUT-SOD was transported in the 30 second interval prior to the end of the experiment. When this time interval was decreased to 15 seconds prior to the administration of the second radiolabelled PUT-SOD, no significant differences in the $V_p$ values were obtained.

compared to the native SOD. The $V_p$ for PUT-SOD at pH 4.7 reached significance which was 2.6-fold greater than the $V_p$ value for native SOD. These values were obtained by the administration of the second isotope at 30 seconds prior to the end of the experiment. Some transport of the $^{131}$I-PUT-SOD is consequently occurring during this 30 second interval. When the second isotope was administered at 15 seconds prior to the end of the experiment, no significant differences were observed for the $V_p$ values for PUT-SOD at pH 4.7.

TABLE 16

PS and $V_p$ of the BBB for SOD and pSOD

| | SOD | PUT-SOD | PUT-SOD vs SOD RI | P | SPD-SOD | SPD-SOD vs SOD RI | P | SPM-SOD | SPM-SOD vs SOD RI | P |
|---|---|---|---|---|---|---|---|---|---|---|
| PS: ml/g/sec × 10$^6$ | | | | | | | | | | |
| Cortex | 1.80 ± 0.09 | 34.75 ± 3.55 | 19.3 | <0.001 | 25.00 ± 0.90 | 13.9 | <0.001 | 6.82 ± 0.95 | 3.8 | NS |
| Caudate-putamen | 1.78 ± 0.11 | 41.92 ± 9.05 | 23.6 | <0.001 | 32.65 ± 2.03 | 18.3 | <0.001 | 7.48 ± 0.93 | 4.2 | NS |
| Hippocampus | 2.15 ± 0.01 | 43.35 ± 3.81 | 20.2 | <0.001 | 28.75 ± 1.39 | 13.4 | <0.001 | 7.98 ± 0.99 | 3.7 | NS |
| Thalamus | 2.71 ± 0.20 | 47.63 ± 3.34 | 17.6 | <0.001 | 34.35 ± 1.42 | 12.7 | <0.001 | 11.22 ± 2.11 | 4.1 | 0.02 |
| Brain Stem | 3.13 ± 0.14 | 56.65 ± 4.40 | 18.1 | <0.001 | 36.85 ± 1.70 | 11.8 | <0.001 | 12.30 ± 1.48 | 3.9 | 0.02 |
| Cerebellum | 2.69 ± 0.11 | 49.75 ± 3.53 | 18.5 | <0.001 | 37.28 ± 1.01 | 13.9 | <0.001 | 10.64 ± 1.32 | 4.0 | 0.02 |
| $V_p$: μl/g | | | | | | | | | | |
| Cortex | 5.77 ± 0.34 | 9.58 ± 0.50 | 1.7 | <0.001 | 7.10 ± 0.31 | 1.2 | NS | 5.80 ± 0.25 | 1.0 | NS |
| Caudate-putamen | 5.76 ± 0.40 | 11.27 ± 0.63 | 2.0 | <0.001 | 8.23 ± 0.40 | 1.4 | <0.05 | 6.47 ± 0.32 | 1.1 | NS |
| Hippocampus | 7.26 ± 0.77 | 11.89 ± 0.71 | 1.6 | <0.05 | 7.73 ± 0.58 | 1.1 | NS | 6.84 ± 0.47 | 0.9 | NS |
| Thalamus | 9.73 ± 0.43 | 15.08 ± 0.96 | 1.5 | <0.01 | 11.23 ± 0.63 | 1.2 | NS | 10.77 ± 1.26 | 1.1 | NS |
| Brain Stem | 13.77 ± 2.10 | 20.83 ± 0.82 | 1.5 | <0.05 | 13.94 ± 1.29 | 1.0 | NS | 13.83 ± 0.40 | 1.0 | NS |
| Cerebellum | 10.20 ± 0.89 | 16.52 ± 0.73 | 1.6 | <0.02 | 12.59 ± 0.90 | 1.2 | NS | 11.45 ± 0.63 | 1.1 | NS |

$\bar{x}$ ± SEM
n = 6
P: ANOVA
NS: not significant (P>0.05)

Figure 8:
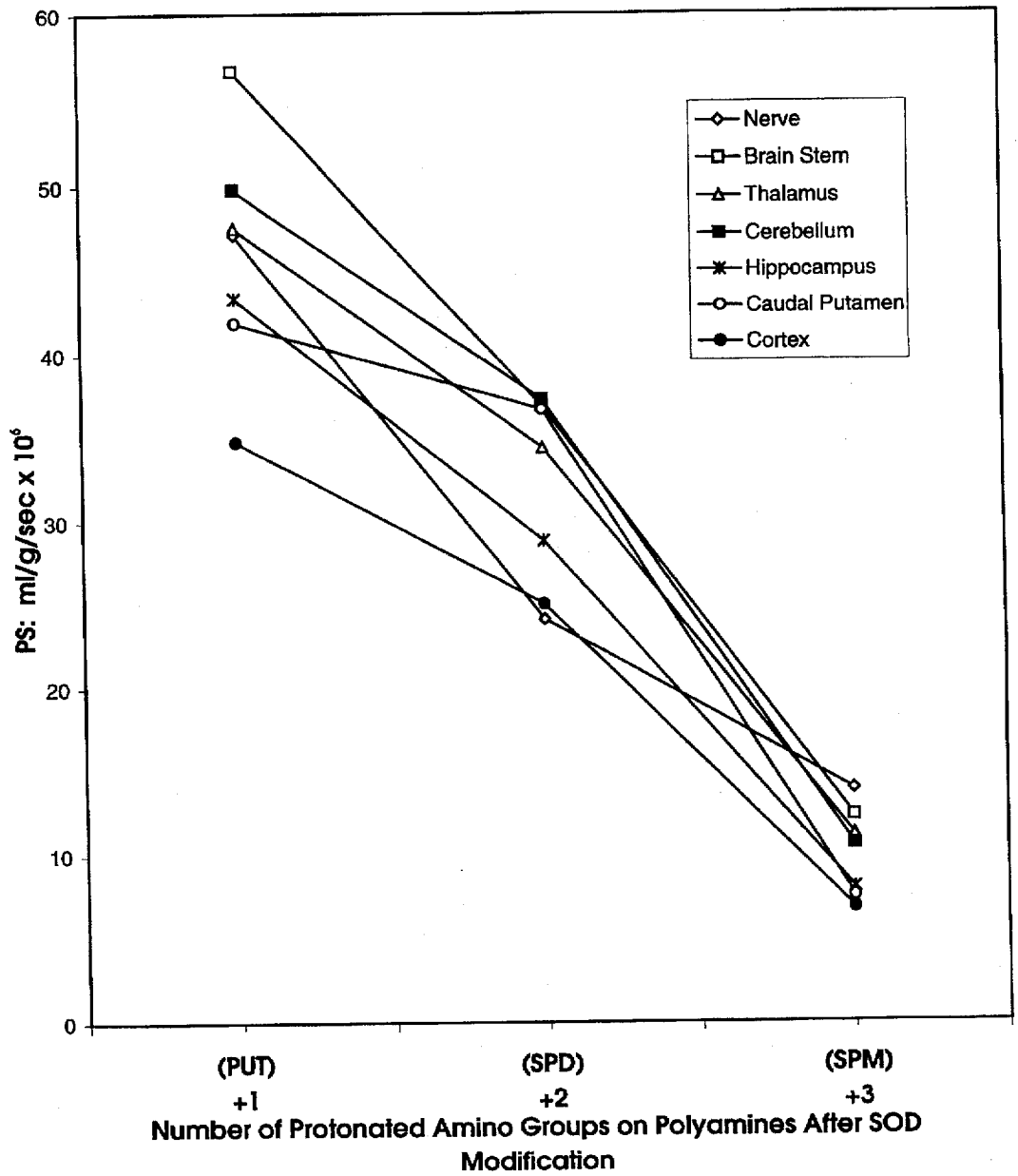
FIG. 8 is a graphical depiction of the inverse relationship of PS with polyamine valency after the modification of SOD with PUT, SPD, and SPM.

The number of protonated amino groups on the three polyamines after protein modification increase in the order of PUT<SPD<SPM, with a corresponding valency of +1, +2, and +3, respectively. FIG. 8 illustrates the relationship of PS values with the increasing number of positive charges in the polyamines for the nerve and different brain regions. As the valency of the protonated amino groups on the polyamines increased, the PS values decreased for the nerve and all brain regions as indicated in Table 15 and Table 16. This relationship has also been demonstrated for PUT-ALB, SPD-ALB, and SPM-ALB. The increase in permeability observed after polyamine modification, therefore, was not solely dependent on the charge associated with the polyamine after modification. This finding, therefore, implies that the observed permeability change, occurs by a mechanism other than simple electrostatic interactions.

(2) Modified at different pH's

The PS and $V_p$ values of the BNB and BBB for SOD and PUT-SOD modified at varied pH are shown in Tables 17 and 18, below. As shown in Table 17, native SOD had a PS value at the BNB of 1.79±0.12×10$^{-6}$ mg/g/sec. Modification of SOD with PUT at pH 7.7 resulted in a 2.8-fold relative increase in PS compared to the native protein; reaction at pH 6.7 demonstrated a significant 7.5-fold increase; reaction at pH 5.7 demonstrated a significant 13.7-fold increase; and reaction at pH 4.7 demonstrated a remarkable 26.4-fold increase compared to native SOD (Table 17). No changes were observed in the $V_p$ values at pH 7.7, 6.7, and 5.7

TABLE 17

PS and Vp of the BNB for SOD and PUT-SOD Modified at Different pH

| | SOD | | PUT-SOD | PUT-SOD vs. SOD | |
|---|---|---|---|---|---|
| | (n = 14) | pH | (n = 12) | RI | P |
| PS: ml/g/sec × 10$^6$ | | | | | |
| | 1.79 ± 0.12 | 7.7 | 5.10 ± 0.79 | 2.8 | NS |
| | | 6.7 | 13.46 ± 1.14 | 7.5 | <0.001 |
| | | 5.7 | 24.48 ± 1.30 | 13.7 | <0.001 |
| | | 4.7 | 47.18 ± 2.10 | 26.4 | <0.001 |
| $V_p$: μl/g | | | | | |
| | 1.87 ± 0.10 | 7.7 | 2.71 ± 0.22 | 1.4 | NS |
| | | 6.7 | 2.81 ± 0.32 | 1.3 | NS |
| | | 5.7 | 2.68 ± 0.34 | 1.4 | NS |
| | | 4.7 | 4.82 ± 0.60 | 2.6 | <0.001 |

$\bar{x}$ ± SEM
P: ANOVA
NS: not significant (P>0.05)

As shown in Table 18, native SOD has PS values at the BBB that ranged from 1.5–3.19×10$^{-6}$ mg/g/see for the six different brain regions. Modification of SOD with PUT at pH 7.7 showed a nonsignificant increase in the PS value for these different brain regions. Modification at pH 6.7 showed significant increases in PS values for the thalamus and cerebellum. When modification was done at pH 5.7, highly significant increases in the PS were observed for all the different brain regions which ranged from 8.8-fold higher for the brain stem to 16-fold higher for the caudate-putamen. Modification of SOD with putrescine at pH 4.7 showed the highest increase in PS values that ranged from $34.75 \times 10^{-6}$ ml/g/sec for the cortex to a high of $56.65 \times 10^{-6}$ ml/g/sec for the brain stem. This represented a highly significant increase in PS values that were 16.9–27.6-fold higher than that of the native SOD. No significant differences were observed in the $V_p$ values in the six different brain regions at pH of 7.7, 6.7, and 5.7. When modified at pH 4.7, a 1.5–2.0 increase in the $V_p$ values was observed for the cortex, caudate-putamen and hippocampus. These values just reached significance in these brain regions which indicates that some of the $^{131}$I-PUT-SOD was transported in the 30 second interval prior to the end of the experiments. Again, when the time interval was decreased to 15 seconds prior to the administration of the second radiolabelled PUT-SOD, no significant differences in the $V_p$ values were obtained.

All of the patents, patent documents and publications cited herein are incorporated by reference.

The invention has been described with reference to various specific and preferred embodiments and techniques. However, it should be understood that many variations and modifications may be made while remaining within the spirit and scope of the invention.

What is claimed is:

1. A method to enhance the ability of a neurologically active compound to penetrate the blood-nerve-barrier or blood-brain-barrier comprising parenterally administering to a mammal in need of treatment with said neurologically active compound, a conjugate consisting of an effective amount of said neurologically active compound linked to a polyamine having a substantial permeability coefficient across the blood-nerve-barrier or blood-brain-barrier.

2. The method of claim 1 wherein the neurologically active compound is selected from the group consisting of a compound acting at a synaptic and/or neuroeffector junctional site, a compound acting on the central or peripheral nervous system, an antioxidant, or a neurotrophic protein.

3. The method of claim 1 wherein the neurologically active compound is an antioxidant or a neurotrophic protein.

4. The method of claim 3 wherein the neurologically active compound is superoxide dismutase or neuronal growth factor.

5. The method of claim 1 wherein the polyamine is selected from the group consisting of putrescine, spermidine and spermine.

6. The method of claim 1 wherein the mammal is a human.

7. The method of claim 1 wherein said conjugate is administered in combination with a pharmaceutically acceptable carrier.

8. The method of claim 7 wherein the pharmaceutically acceptable carrier is a solid.

9. The method of claim 7 wherein the pharmaceutically acceptable carrier is a liquid.

10. A pharmaceutical composition comprising a neurologically active compound linked to a polyamine in combination with a pharmaceutically acceptable carrier.

11. The pharmaceutical composition of claim 10 which is adapted for parenteral administration.

TABLE 18

PS and $V_p$ of the BBB for SOD and PUT-SOD Modified at Different pH

| | SOD (n = 7) | PUT-SOD: pH 7.7 | RI | P | PUT-SOD: pH 6.7 | RI | P | PUT-SOD: pH 5.7 | RI | P | PUT-SOD: pH 4.7 | RI | P |
|---|---|---|---|---|---|---|---|---|---|---|---|---|---|
| PS: ml/g/sec × $10^6$ | | | | | | | | | | | | | |
| Cortex | 1.81 ± 0.06 | 2.31 ± 0.07 | 1.3 | NS | 7.26 ± 0.48 | 4.0 | NS | 17.85 ± 1.18 | 9.9 | <0.001 | 34.75 ± 3.55 | 19.2 | <0.001 |
| Caudate-putamen | 1.52 ± 0.07 | 2.70 ± 0.17 | 1.8 | NS | 8.00 ± 0.54 | 5.3 | NS | 24.25 ± 2.73 | 16.0 | <0.001 | 41.92 ± 3.69 | 27.6 | <0.001 |
| Hippocampus | 1.98 ± 0.08 | 2.80 ± 0.14 | 1.4 | NS | 8.59 ± 0.43 | 4.3 | NS | 21.95 ± 1.62 | 11.1 | <0.001 | 43.35 ± 3.81 | 21.9 | <0.001 |
| Thalamus | 2.61 ± 0.15 | 3.53 ± 0.10 | 1.4 | NS | 10.19 ± 0.51 | 3.9 | <0.05 | 25.62 ± 2.08 | 9.8 | <0.001 | 47.63 ± 3.34 | 18.2 | <0.001 |
| Brain Stem | 3.19 ± 0.13 | 4.09 ± 0.10 | 1.3 | NS | 10.78 ± 0.58 | 3.4 | NS | 28.22 ± 2.07 | 8.8 | <0.001 | 56.65 ± 4.40 | 17.8 | <0.001 |
| Cerebellum | 2.94 ± 0.14 | 3.82 ± 0.11 | 1.3 | NS | 10.67 ± 0.50 | 3.6 | <0.05 | 27.37 ± 1.84 | 9.3 | <0.001 | 49.75 ± 3.53 | 16.9 | <0.001 |
| $V_p$: μl/g | | | | | | | | | | | | | |
| Cortex | 6.13 ± 0.34 | 6.13 ± 0.34 | 1.1 | NS | 6.09 ± 0.44 | 1.0 | NS | 5.28 ± 0.66 | 0.9 | NS | 9.58 ± 0.50 | 1.6 | <0.001 |
| Caudate-putamen | 5.62 ± 0.23 | 6.44 ± 0.41 | 1.1 | NS | 5.95 ± 0.67 | 1.1 | NS | 6.47 ± 0.88 | 1.2 | NS | 11.27 ± 0.63 | 2.0 | <0.001 |
| Hippocampus | 7.94 ± 0.25 | 8.57 ± 0.80 | 1.1 | NS | 7.69 ± 0.68 | 1.0 | NS | 6.20 ± 0.82 | 0.8 | NS | 11.89 ± 0.71 | 1.5 | <0.01 |
| Thalamus | 12.83 ± 1.97 | 12.11 ± 1.05 | 0.9 | NS | 9.95 ± 0.84 | 0.8 | NS | 8.44 ± 1.28 | 0.7 | NS | 15.08 ± 0.86 | 1.2 | NS |
| Brain Stem | 16.26 ± 1.22 | 15.17 ± 0.88 | 0.9 | NS | 12.94 ± 1.38 | 0.8 | NS | 12.10 ± 1.72 | 0.7 | NS | 20.83 ± 0.82 | 1.3 | NS |
| Cerebellum | 14.61 ± 1.09 | 13.17 ± 1.15 | 0.9 | NS | 11.30 ± 0.87 | 0.8 | NS | 9.13 ± 0.93 | 0.6 | <0.01 | 16.52 ± 0.73 | 1.1 | NS |

$\bar{x}$ ± SEM
n = 6
P: ANOVA

12. The pharmaceutical composition of claim 11 wherein the pharmaceutically acceptable carrier is a liquid vehicle.

13. The pharmaceutical composition of claim 10 wherein the neurologically active compound is selected from the group consisting of a compound acting at a synaptic and/or neuroeffector junctional site, a compound acting on the central or peripheral nervous system, an antioxidant, or a neurotrophic protein.

14. The pharmaceutical composition of claim 10 wherein the neurologically active compound is an antioxidant or a neurotrophic protein.

15. The pharmaceutical composition of claim 14 wherein the neurologically active compound is superoxide dismutase or neuronal growth factor.

16. The pharmaceutical composition of claim 10 wherein the polyamine is selected from the group consisting of putrescine, spermidine or spermine.

17. An isolated and purified composition consisting of a neurologically active compound linked to a polyamine, wherein the polyamine is present in an amount effective to increase the ability of the composition to cross the brain-nerve barrier or blood-brain barrier of a mammal to which said composition is administered.

18. The composition of claim 17 wherein the neurologically active compound is selected from the group consisting of a compound acting at a synaptic and/or neuroeffector junctional site, a compound acting on the central or peripheral nervous system, an antioxidant, or a neurotrophic protein.

19. The composition of claim 18 wherein the neurologically active compound is an antioxidant or a neurotrophic protein.

20. The composition of claim 19 wherein the neurologically active compound is neuronal growth factor or superoxide dismutase.

21. The composition of claim 17 wherein the polyamine is selected from the group consisting of putrescine, spermine, or spermidine.

* * * * *

UNITED STATES PATENT AND TRADEMARK OFFICE
CERTIFICATE OF CORRECTION

PATENT NO. : 5,670,477
DATED : September 23, 1997
INVENTOR(S) : Joseph F. Poduslo et al.

It is certified that error appears in the above-identified patent and that said Letters Patent is hereby corrected as shown below:

On the title page item,

[75] front page, please delete addresses from inventors and insert --both from Rochester, Minnesota--.

At [54] in the title, please delete "Bariers" and insert --Barriers--.

Column 1, line 3, please delete "Bariers" and insert --Barriers--.

Column 20, line 20, please delete "0.09" and insert --0.02--.

Column 23, line 15, please delete "(CHAT)" and insert --(ChAT)--.

Column 26, line 26, please delete "BNB" and insert --BBB--.

Column 27, line 18, please delete "BNB" and insert --BBB--.

Column 28, line 3, please delete "BNB" and insert --BBB--.

Column 32, line 55, please delete "1.3" and insert --1.5--.

Signed and Sealed this

Thirteenth Day of October 1998

*Attest:*

BRUCE LEHMAN

*Attesting Officer*   Commissioner of Patents and Trademarks